United States Patent [19]

Tominaga et al.

[11] Patent Number: 4,514,401
[45] Date of Patent: Apr. 30, 1985

[54] CARBOSTYRIL DERIVATIVES

[75] Inventors: Michiaki Tominaga; Yung-hsiung Yang; Hidenori Ogawa; Kazuyuki Nakagawa, all of Tokushima, Japan

[73] Assignee: Otsuka Pharmaceutical Co., Ltd., Tokyo, Japan

[21] Appl. No.: 407,099

[22] Filed: Aug. 11, 1982

Related U.S. Application Data

[63] Continuation of Ser. No. 265,501, May 20, 1981, abandoned.

[30] Foreign Application Priority Data

Sep. 1, 1981 [JP] Japan .................. 56-137984
Dec. 25, 1981 [JP] Japan .................. 56-210368

[51] Int. Cl.³ .................. C07D 215/00; A61K 31/47
[52] U.S. Cl. .................. 514/253; 544/363; 544/377; 544/379
[58] Field of Search .................. 544/363, 377, 379; 424/250

[56] References Cited

FOREIGN PATENT DOCUMENTS

| | | | |
|---|---|---|---|
| 51-18771 | 10/1976 | Japan | 544/363 |
| 52-282 | 1/1977 | Japan | 544/363 |
| 52-283 | 1/1977 | Japan | 544/363 |
| 53-12515 | 5/1978 | Japan | 544/363 |
| 54-16478 | 2/1979 | Japan | 544/363 |
| 56-16470 | 2/1981 | Japan | 544/363 |
| 2071094 | 9/1981 | United Kingdom | 544/363 |
| 2094789 | 9/1982 | United Kingdom | 544/363 |

Primary Examiner—Nicholas S. Rizzo
Assistant Examiner—S. A. Gibson
Attorney, Agent, or Firm—Finnegan, Henderson, Farabow, Garrett & Dunner

[57] ABSTRACT

Novel carbostyril derivatives represented by the general formula (1),

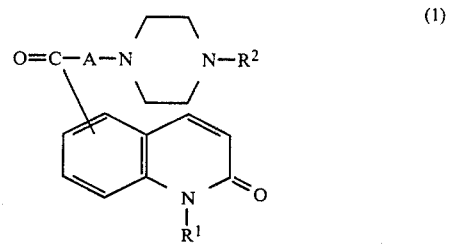

wherein $R^1$ is a hydrogen atom, a lower alkyl group, a lower alkenyl group, a lower alkynyl group or a phenyl-lower alkyl group; $R^2$ is a lower alkanoyl group, a lower alkoxycarbonyl group, a furoyl group, a lower alkane-sulfonyl group, a substituted benzoyl group, a substituted phenyl-lower alkenylcarbonyl group, a phenoxy-lower alkyl group, or a substituted phenylsulfonyl group; A is a lower alkylene group; the carbon-carbon bond between 3- and 4-positions in the carbostyril skeleton is a single or double bond; and the substituted position of the side-chain of the formula,

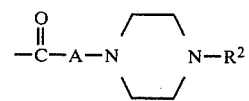

may be of 5-, 6-, 7- or 8-position in the carbostyril skeleton; and acid addition salts thereof.

The carbostyril derivatives of the general formula (1) of the present invention and acid addition salts thereof have myocardial contraction increasing activity (positive inotropic activity), coronary blood flow increasing activity and hypotensive activity. They are useful as cardiotonics for curing various heart diseases such as congestive heart failure, mitralism, auricular fibrillation, auricular flutter, paroxysmal atrial tachycardia and the like.

17 Claims, No Drawings

CARBOSTYRIL DERIVATIVES

The present invention relates to a novel carbostyril derivative and a salt thereof, processes for preparing the same and a cardiotonic composition containing the same as the active ingredient.

A carbostyril derivative and a salt thereof according to the present invention is represented by the following general formula (1),

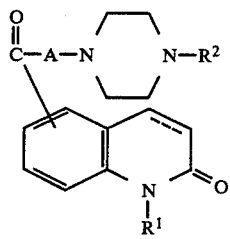

wherein $R^1$ is a hydrogen atom, a lower alkyl group, a lower alkenyl group, a lower alkynyl group or a phenyl-lower alkyl group; $R^2$ is a lower alkanoyl group, a lower alkoxycarbonyl group, a furoyl group, a lower alkanesulfonyl group, a benzoyl group (which may have 1 to 3 substituents selected from the group consisting of a lower alkyl group, a lower alkoxy group, a halogen atom, a cyano group, an amino group and a nitro group on the phenyl ring, or may have a lower alkylenedioxy group as the substituent on the phenyl ring), a phenyl-lower alkenylcarbonyl group (which may have 1 to 3 lower alkoxy groups as the substituents on the phenyl ring), a phenoxy-lower alkyl group, or a phenylsulfonyl group (which may have a lower alkyl group as the substituent on the phenyl ring); A is a lower alkylene group; the carbon-carbon bond between 3- and 4-positions in the carbostyril skeleton is a single or double bond; and the substituted position of the side-chain of the formula,

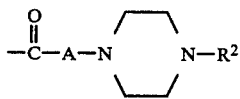

may be of 5-, or 6-, 7- or 8-position in the carbostyril skeleton.

Carbostyril derivative represented by the general formula (1) of the present invention includes a pharmacologically acceptable acid-addition salt thereof.

A compound represented by the general formula (1) of the present invention and pharmacologically acceptable salt thereof have myocardial contraction increasing activity (positive inotropic activity), coronary blood flow increasing activity and hypotensive activity, and thus they are useful as cardiotonics for curing various heart diseases such as congestive heart failure, mitralism, auricular fibrillation, auricular flutter, paroxysmal atrial tachycardia and the like. Specifically, carbostyril derivative and salt thereof represented by the general formula (1) have excellent effects in positive inotropic activity, coronary blood flow increasing activity and hypotensive activity, while they are characterized that as they have less toxicities to the heart such as very weak heart beat increasing activity.

Some carbostyril derivatives having useful pharmacological activities, such as bronchiectatic activity, antihistaminic activity, anti-hypertensive activity and central nervous system controlling activity are known in prior art literatures, for example:

(a) Japanese Patent Application Kokai (Laid-open) No. Sho 53-12515 (1978)
(b) Japanese Patent Application Kokai (Laid-open) No. Sho 51-118771 (1976)
(c) Japanese Patent Application Kokai (Laid-open) No. Sho 54-16478 (1979)
(d) Japanese Patent Application Kokai (Laid-open) No. Sho 52-282 (1977)
(e) Japanese Patent Application Kokai (Laid-open) No. Sho 52-283 (1977)
(f) Japanese Patent Application Kokai (Laid-open) No. Sho 56-16470 (1981) and
(g) DE-OS No. 3107601

These prior literatures disclose compounds having chemical structural formulas, especially the chemical structural formulas of the side-chain attached to the carbostyril skeleton, are similar to that of the carbostyril derivatives of the general formula (1) of the present invention, but the pharmacological activities thereof are quite different from those of shown by the carbostyril derivatives of the present invention.

On the other hand, the pharmacological activity of the compounds disclosed in (h) Belgian Pat. No. 890942 (Registered on Nov. 13, 1981) is similar to that of carbostyril derivative of the present invention, but the features and the chemical structural formulas are different from those of carbostyril derivatives of the present invention.

Carbostyril derivative and salt thereof represented by the general formula (1) of the present invention indeed have a chemical structure similar to those of the compounds disclosed in the above-mentioned prior art references, but the former derivative and salt thereof are not, in fact, substantially included in the prior art compounds.

An object of the present invention is to provide novel carbostyril derivative and salt thereof represented by the general formula (1), having cardiotonic activities.

Another object of the present invention is to provide processes for preparing said carbostyril derivative and salt thereof represented by the general formula (1).

Further object of the present invention is to provide a cardiotonic composition containing said carbostyril derivative and salt thereof represented by the general formula (1) as the active ingredient.

The specific examples of the groups as defined in the symbol "$R^1$" in the general formula (1), they are shown as follows:

The expression of "a lower alkyl group" means "a straight- or branched-chain alkyl group having 1 to 6 carbon atoms", and the examples including methyl, ethyl, propyl, isopropyl, butyl, tert-butyl, pentyl, hexyl or the like.

The expression of "a lower alkenyl group" means "a straight- or branched-chain alkenyl group having 2 to 6 carbon atoms", and the examples including vinyl, allyl, 2-butenyl, 3-butenyl, 1-methylallyl, 2-pentenyl, 2-hexenyl or the like.

The expression of "a lower alkynyl group" means "a straight- or branched-chain alkynyl group having 2 to 6 carbon atoms", and the examples including ethynyl, 2-propynyl, 2-butynyl, 3-butynyl, 1-methyl-2-propynyl, 2-pentynyl, 2-hexynyl or the like.

The expression of "a phenyl-lower alkyl group" means "a straight- or branched-chain alkyl group (having 1 to 6 carbon atoms) having a phenyl group as the substituent", and the examples including benzyl, 2-phenylethyl, 1-phenylethyl, 3-phenylpropyl, 4-phenylbutyl, 1,1-dimethyl-2-phenylethyl, 5-phenylpentyl, 6-phenylhexyl, 2-methyl-3-phenylpropyl or the like.

The specific examples of the groups as defined in the symbol "$R^2$" in the general formula (1) are shown as follows:

The expression of "a lower alkanoyl group" means "a straight- or branched-chain alkanoyl group having 1 to 6 carbon atoms", and the examples including formyl, acetyl, propionyl, butyryl, isobutyryl, pentanoyl, tert-butylcarbonyl, hexanoyl or the like.

The expression of "a lower alkoxycarbonyl group" means "a straight- or branched-chain alkoxycarbonyl group having 1 to 6 carbon atoms in the alkoxy moiety", and the examples including methoxycarbonyl, ethoxycarbonyl, propoxycarbonyl, isopropoxycarbonyl, butoxycarbonyl, tert-butoxycarbonyl, petyloxycarbonyl, hexyloxycarbonyl or the like.

The expression of "a lower alkanesulfonyl group" means "a straight- or branched-chain alkanesulfonyl group having 1 to 6 carbon atoms in the alkena moiety", and the examples including methanesulfonyl, ethanesulfonyl, propanesulfonyl, isopropanesulfonyl, butanesulfonyl, tert-butanesulfonyl, pentanesulfonyl, hexanesulfonyl or the like.

The expression of "a benzoyl group (which may have 1 to 3 substituents, on the phenyl ring, selected from the group consisting of a lower alkyl group, a lower alkoxy group, a halogen atom, a cyano group, an amino group and a nitro group, or may have a lower alkylenedioxy group as the substituent on the phenyl ring)" means "a benzoyl group which may have 1 to 3 substituents, on the phenyl ring, selected from the group consisting of a straight- or branched-chain alkyl group (having 1 to 6 carbon atoms), a straight- or branched-chain alkoxy group (having 1 to 6 carbon atoms), a halogen atom, a cyano group, an amino group and a nitro group, or may have a straight- or branched-chain alkylenedioxy group (having 1 to 4 carbon atoms) as the substituent on the phenyl ring, and examples including benzoyl, 2-, 3- or 4-chlorobenzoyl, 2-, 3- or 4-fluorobenzoyl, 2-, 3- or 4-bromobenzoyl, 2-, 3- or 4-iodobenzoyl, 3,5-dichlorobenzoyl, 2,6-dichlorobenzoyl, 3,4-dichlorobenzoyl, 3,4-difluorobenzoyl, 3,5-dibromobenzoyl, 3,4,5-trichlorobenzoyl, 2-, 3- or 4-methylbenzoyl, 2-, 3- or 4-ethylbenzoyl, 3-isopropylbenzoyl, 4-hexybenzoyl, 3,4-dimethylbenzoyl, 2,5-dimethylbenzoyl, 3,4,5-trimethylbenzoyl, 2-, 3- or 4-methoxybenzoyl, 2-, 3- or 4-ethoxybenzoyl, 4-isopropoxybenzoyl, 4-hexyloxybenzoyl, 3,4-dimethoxybenzoyl, 3,4-diethoxybenzoyl, 3,4,5-trimethoxybenzoyl, 2,5-dimethoxybenzoyl, 2-, 3- or 4-nitrobenzoyl, 2,4-dinitrobenzoyl, 2-, 3- or 4-aminobenzoyl, 2,4-diaminobenzoyl, 2,3-diaminobenzoyl, 3,4-diaminobenzoyl, 2,5-diaminobenzoyl, 3,4,5-triaminobenzoyl, 2-, 3- or 4-cyanobenzoyl, 2,4-dicyanobenzoyl, 3,4-methylenedioxybenzoyl, 3,4-ethylenedioxybenzoyl, 2,3-methylenedioxybenzoyl, 3-methyl-4-chlorobenzoyl, 2-chloro-6-methylbenzoyl, 2-methoxy-3-chlorobenzoyl or the like.

The expression of "a phenyl-lower alkenylcarbonyl group (which may have 1 to 3 lower alkoxy groups as the substitutents on the phenyl ring)" means "a straight- or branched-chain alkenylcarbonyl group (having 3 to 6 carbon atoms) having a phenyl group which may have 1 to 3 straight- or branched-chain alkoxy groups (having 1 to 6 carbon atoms) as the substituents on the phenyl ring" and the examples including cinnamoyl, 4-phenyl-3-butenoyl, 4-phenyl-2-butenoyl, 5-phenyl-4-pentenoyl, 5-phenyl-3-pentenoyl, 5-phenyl-2-pentenoyl, 6-phenyl-5-hexenoyl, 6-phenyl-4-hexenoyl, 6-phenyl-3-hexenoyl, 6-phenyl-2-hexenoyl, 2-methyl-4-phenyl-3-butenylcarbonyl, 2-methylcinnamoyl, 2-, 3- or 4-methoxycinnamoyl, 2-, 3- or 4-ethoxycinnamoyl, 2-, 3- or 4-propoxycinnamoyl, 2-butoxycinnamoyl, 3-(tert-butoxy)cinnamoyl, 4-pentyloxycinnamoyl, 3-hexyloxycinnamoryl, 3,5-dimethoxycinnamoyl, 2,6-dimethoxycinnamoyl, 3,4-dimethoxycinnamoyl, 3,4-diethoxycinnamoyl, 3,5-diethoxycinnamoyl, 3,4,5-trimethoxycinnamoyl, 4-ethoxyphenyl-3-butenoyl, 4-(3-tert-butoxyphenyl)-2-butenoyl, 5-(4-hexyloxyphenyl)-4-pentenoyl, 6-(3,4-dimethoxyphenyl)-5-hexenoyl, 2-methyl-(2,5-diethoxyphenyl)cinnamoyl, 1-methyl-(3-methoxyphenyl)cinnamoyl, 6-(3,4,5-triethoxyphenyl)-3-hexenylcarbonyl or the like.

The expression of "a phenoxy-lower alkyl group" means "a straight- or branched-chain alkyl group (having 1 to 6 carbon atoms) having a phenoxy group as the substituent", the examples including phenoxymethyl, 2-phenoxyethyl, 2-phenoxypropyl, 3-phenoxypropyl, 1-methyl-2-phenoxyethyl, 2-phenoxybutyl, 3-phenoxybutyl, 4-phenoxybutyl, 1,1-dimethyl-2-phenoxybutyl, 2-phenoxypentyl, 3-phenoxypentyl, 4-phenoxyhexy or the like.

The expression of "a phenylsulfonyl group (which may have a lower alkyl group as the substituent on the phenyl ring)" means "a phenylsulfonyl group which may have 1 to 3 atraight- or branched-chain alkyl groups (having 1 to 6 carbon atoms) as the substituents on the phenyl ring", and the examples including phenylsulfonyl, p-toluenesulfonyl, 2-methylphenylsulfonyl, 3-ethylphenylsulfonyl, 4-propylphenylsulfonyl, 2-butylphenylsulfonyl, 3-tert-butylphenylsulfonyl, 3,4-dimethylphenylsulfonyl, 3,4,5-trimethylphenylsulfonyl, 4-pentylphenylsulfonyl, 2-hexylphenylsulfonyl or the like.

As to the specific examples of the lower alkylene group defined in the symbol "A" in the genral formula (1), there can be exemplified a straight- or branched-chain alkylene group having 1 to 6 carbon atoms, such as methylene, ethylene, trimethylen, 2-methyltrimethylene, 2,2-dimethyltrimethylene, 1-methyltrimethylene, methylmethylene, ethylmethylene, tetramethylene, pentamethylene, hexamethylene or the like.

A carbostyril derivative and a salt thereof represented by the general formula (1) of the present invention can be prepared by methods of the reaction process formulas as mentioned below:

REACTION PROCESS FORMULA-1

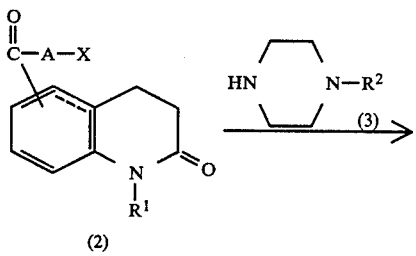

(2)

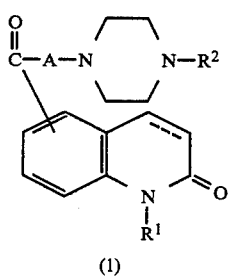

(1)

wherein $R^1$, $R^2$, A, the carbon-carbon bond between 3- and 4-positions in the carbostyril skeleton, and the substituted position of the side-chain in the carbostyril skeleton are the same as defined above; X is a halogen atom.

Thus, carbostyril derivative represented by the general formula (1) of the present invention is prepared by reacting a compound of the general formula (2) some of which are novel and other compounds are known as disclosed in German Pat. No. 3,107,601 with a piperazine derivative represented by the general formula (3).

The reaction of a compound of the general formula (2) with a piperazine derivative of the general formula (3) is carried out in the absence of a solvent, or in the presence of a common inert solvent, at a temperature condition from a room temperature to 200° C., preferably at a room temperature to 120° C., for 1 to 24 hours. As to the inert solvent used in this reaction, an ether such as dioxane, tetrahydrofuran, ethyleneglycol dimethyl ether, diethyl ether or the like; an aromatic hydrocarbon such as benzene, toluene or xylene or the like; a lower alcohol such as methanol, ethanol, isopropanol or the like; a polar solvent such as dimethylformamide, dimethyl sulfoxide, hexamethylphosphoric triamide, acetone, acetonirile or the like can be used.

The above-mentioned reaction can advantageously be carried out by using a basic compound as the deacidifying agent. As to the basic compound, a piperazine derivative as used for the starting material is included in the basic compound, therefore when a piperazine derivative is used in an excess amount, other basic compound is not necessarily be used. On the other hand, as to the basic compound, an inorganic basic compound such as potassium carbonate, sodium carbonate, sodium hydroxide, sodium bicarbonate, sodium amide, sodium hydride or the like, a tertiary amine such as triethylamine, tripropylamine, pyridine, quinoline or the like can be used.

The above-mentioned reaction can be carried out, if necessary, by adding an alkali metal iodide such as potassium iodide, sodium iodide or the like, or hexamethylphosphoric triamide as a reaction promoter.

The ratio of the amount of a compound represented by the general formula (2) to the amount of a piperazine derivative represented by the general formula (3) in the above-mentioned reaction is not specifically restricted, and the ratio can be selected from a wide range, generally, an equimolar amount to an excess amount, preferably an equimolar amount to 5 times the molar quantity of the latter may be used to the former.

Some of the piperazine derivative represented by the general formula (3) as used for the starting material include novel compounds, and said piperazine derivative may be prepared by using piperazine in place of a carbostyril derivative represented by the general formula (4) as mentioned in the following reaction process formulas-2 and -3.

REACTION PROCESS FORMULA-2

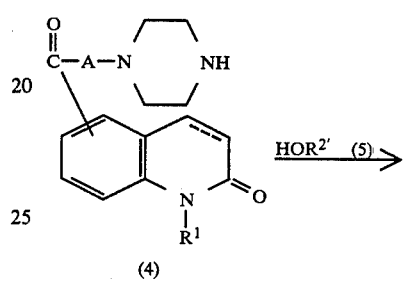

(4)

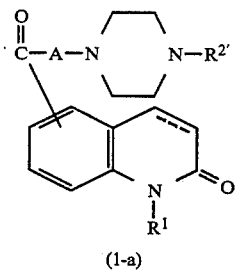

(1-a)

wherein A and the carbon-carbon bond between 3- and 4-positions in the carbostyril skeleton, as well as the substituted position of the side-chain are the same as defined as above; $R^{2'}$ is a lower alkanoyl group, a lower alkoxycarbonyl group, a furoyl group, a benzoyl group (which may have 1 to 3 substituents selected from the group consisting of a lower alkyl group, a lower alkoxy group, a halogen atom, a cyano group, an amino group and a nitro group, on the phenyl ring, or may have a lower alkylenedioxy group as the substituent on the phenyl ring), or a phenyl-lower alkenylcarbonyl group (which may have 1 to 3 lower alkoxy groups as the substituents on the phenyl ring).

Thus, among the objective compounds of the present invention, carbostyril derivative represented by the general formula (1-a) can be prepared by reacting a carobstyril derivative represented by the general formula (4) (which is known in German Pat. No. 3,107,601) with a carboxylic acid or an activated compound of its carboxyl group represented by the general formula (5).

Above-mentioned reaction can be carried out by a method commonly used in amide-bond formation reaction. As to the amide-bond formation reation, there are exemplified as follows:

(a) a mixed acid anhydride method, that is a method by reacting a carboxylic acid (5) with an alkylhalocarboxylic acid to obtain a mixed acid anhydride, then reacting said mixed acid anhydride with a compound of the general formula (4);

(b) an activated ester method, that is a method by converting a carboxylic acid (5) into an activated ester for example, p-nitrophenyl ester, N-hydroxysuccinimide ester, 1-hydroxybenzotriazole ester or the like, then reacting said activated ester with a compound of the general formula (4);

(c) a carbodiimide method, that is a method by condensing a carboxylic acid (5) with a compound of the general formula (4) in the presence of an activating agent, for example dicyclohexylcarbodiimide, carbonyldiimidazole or the like;

(d) other methods, for example, a method by converting a carboxylic acid (5) into a carboxylic acid anhydride by using a dehydrating agent for example, acetic anhydride, then reacting said carboxylic acid anhydride with a compound of the general formula (4); or a method by reacting an ester of a carboxylic acid (5) of a lower alcohol, with a compound of the general formula (4) under a high pressure and at an elevated temperature; or a method by converting a carboxylic acid (5) into a carboxylic acid halide, (acid halide), then reacting said acid halide with a compound of the general formula (4); or a method by activating a carboxylic acid (5) with a phosphorous compound for example triphenylphosphine, diethylchlorophosphate or the like, then reacting said activated compound with a derivative represented by the general formula (4); and the like.

The mixed acid anhydride used in the method (a) mentioned above can be prepared by a conventional Schotten-Baumann reaction, and a compound of the general formula (1-a) is prepared by reacting a derivative of the general formula (4) with said mixed acid anhydride without being separated from the Schotten-Baumann reaction system. The Schotten-Baumann reaction is generally carried out in the presence of a basic compound. As to the basic compound, any compound usually used in Schotten-Baumann reaction can also be used, for example, an organic base such as triethylamine, trimethylamine, pyridine, dimethylaniline, N-methylmorpholine, 1,5-diazabicyclo(4,3,0)nonene-5 (DBN), 1,5-diazabicyclo(5,4,0)undecene-5 (DBU), 1,4-diazabicyclo(2,2,2)octane (DABCO) or the like; an inorganic basic compound such as potassium carbonate, sodium carbonate, potassium bicarbonate, sodium bicarbonate or the like can be exemplified. Said reaction is carried out at −20° to 100° C., preferably at 0° to 50° C., and the reaction time is about 5 minutes to 10 hours, preferably, 5 minutes to 2 hours.

The reaction of the mixed acid anhydride thus obtained with a derivative of the general formula (4) is carried out at a temperature of about −20° to 150° C., preferably at about 10° to 50° C., for about 5 minutes to 10 hours, preferably for about 5 minutes to 5 hours. The reaction of mixed acid anhydride method is generally carried out in a solvent. As to the solvent used for this reaction, any solvent used for the reaction of mixed acid anhydride method can also be used, specifically, a halogenated hydrocarbon such as methylene chloride, chloroform, dichloroethane or the like, an aromatic hydrocarbon such as benzene, toluene, xylene or the like, an ether such as diethyl ether, tetrahydrofuran, dimethoxyethane or the like, an ester such as methyl acetate, ethyl acetate or the like, an aprotic polar solvent such as N,N-dimethylformamide, dimethyl sulfoxide, hexamethylphosphoric triamide or the like can be exemplified.

As to the alkylhalocarboxylic acid used in the mixed acid anhydride, methyl chloroformate, methyl bromformate, ethyl chloroformate, ethyl bromformate, isobutyl chloroformate or the like can be exemplified.

The ratio of the amount of a carboxylic acid (5) to the amount of an alkylhalocarboxylic acid and a derivative of the general formula (4) in the above-mentioned reaction is generally at least an equimolar quantity, preferably about 1 to 2 times the molar quantity of the latter may be used to the former.

In carrying out the reaction of the carboxylic acid halide with a derivative of the general formula (4) in the above-mentioned method (d), the reaction is carried out in a suitable solvent in the presence of a basic compound. As to the basic compound, any basic compound known in the art can be used, for example a basic compound used in Schotten-Baumann reaction can also be used, furthermore sodium hydroxide, potassium hydroxide, sodium hydride, potassium hydride or the like can be exemplified. As to the solvent, any solvent used in Schotten-Baumann reaction can also be used, furthermore, an aprotic polar solvent such as pyridine, acetone, acetonitrile or the like, or a mixed solvent of two or more above-mentioned solvents can be exemplified.

The ratio of the amount of the carboxylic acid halide to the amount of a derivative of the general formula (4) is not specifically restricted and can be selected from a wide range, and generally at least an equimolar quantity, preferably an equimolar quantity to 5 times the molar quantity of the former can be used to the latter.

The reaction is generally carried out at about −20° to 180° C., preferably at 0° to 150° C., and the reaction is completed for about 5 minutes to 30 hours.

REACTION PROCESS FORMULA-3

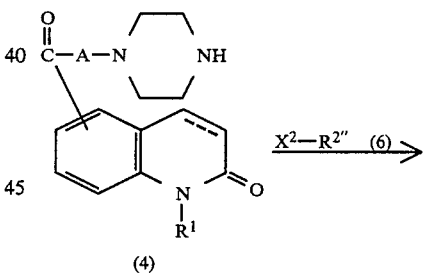

(4)

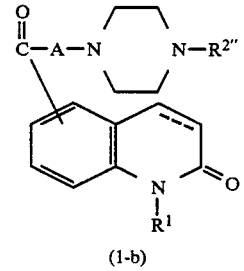

(1-b)

wherein $R^1$, A, the carbon-carbon bond between 3- and 4-positions in the carbostyril skeleton and the substituted position of the side-chain are the same as defined above; $R^{2''}$ is a phenoxy-lower alkyl group, a lower alkanesulfonyl group or a phenylsulfonyl group (which may have a lower alkyl group as the substituent on the phenyl ring); and $X^2$ is a halogen atom.

Thus, among the desired compounds of the present invention, derivative represented by the general formula (1-b) can also be prepared by reacting a known carbostyril derivative of the general formula (4) with a compound represented by the general formula (6).

The reaction of a derivative of the general formula (4) with a compound of the general formula (6) can be carried out under a condition similar to that of in the reaction of a derivative of the general formula (4) with the carboxylic acid halide as explained in detail in the reaction process formula-2.

Furthermore, the desired carbostyril derivative represented by the general formula (1) can also be prepared by methods as mentioned below:

REACTION PROCESS FORMULA-4 mula (2) with a compound of the general formula (7) or a compound of the general formula (8) or a compound of the general formula (8'), and thus obtained compound (9) is then debenzylated, deacylated or dealkylated followed by reacted with a compound of the general formula (11).

In the above-mentioned reaction, the reaction of a compound of the general formula (2) with a compound of the general formula (7), (8) or (8') can be carried out under conditions similar to those used in the reaction of a compound of the general formula (2) with a piperazine derivative of the general formula (3) as shown in the reaction process formula-1.

The debenzylation reaction of a compound of the general formula (9) obtained in the above-mentioned reaction can be carried out under conditions of conven-

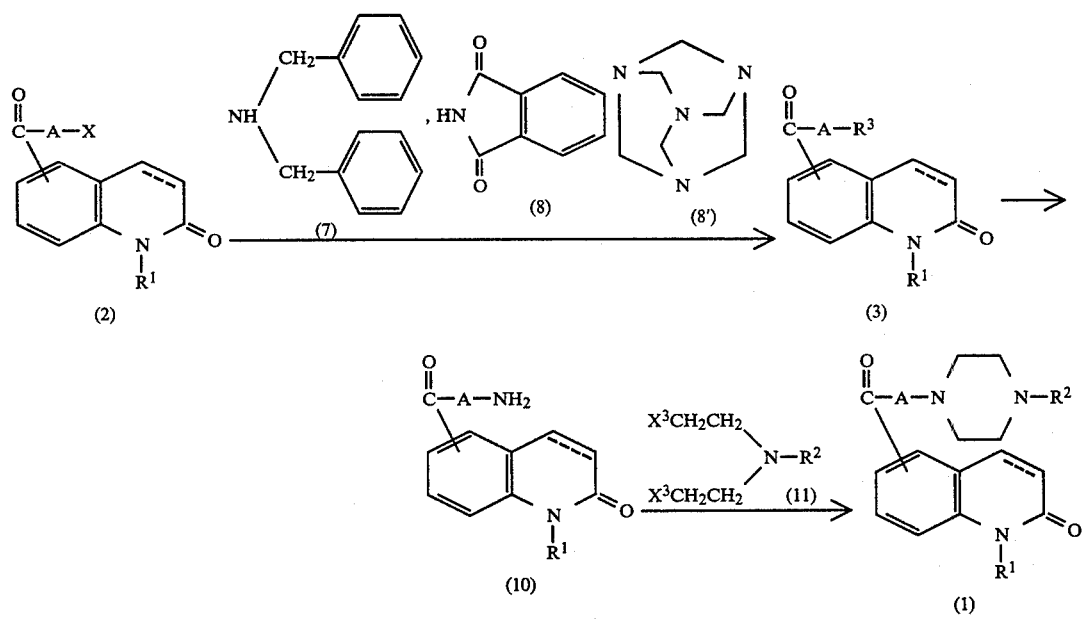

wherein $R^1$, $R^2$, A, X, the carbon-carbon bond in the 3- and 4-positions in the carbostyril skeleton, and the substituted position of the side-chain are the same as defined above; $R^3$ is a group of the formula,

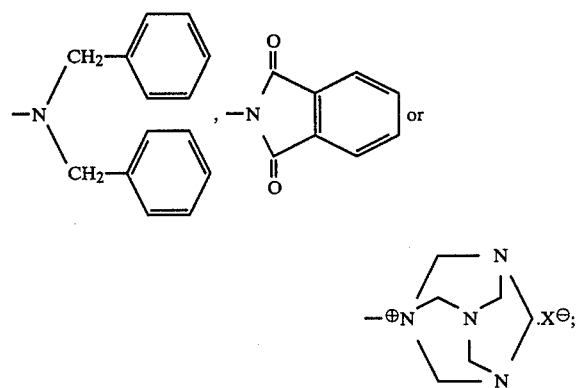

$X^3$ is a halogen atom, a lower alkanesulfonyloxy group, an aralkylsulfonyloxy group or a hydroxy group.

The desired compound of the present invention is prepared by reacting a compound of the general fortional de-N-benzylation reaction. Specifically, the reaction can be carried out in a suitable solvent, in the presence of a catalyst, for example palladium-carbon, palladium black or the like, at a temperature of from 0° C. to a room temperature for about 0.5 to 2 hours. As to the solvent used in the reaction, water, a lower alcohol such as methanol, ethanol, isopropanol or the like, an ether such as dioxane, tetrahydrofuran or the like, acetic acid or the like can be used.

The deacylation or dealkylation reaction of a compound of the general formula (9) obtained in the above-mentioned reaction can be carried out by a method similar to that used in a conventional hydrolysis reaction. For example, the hydrolysis reaction can be carried out in a solvent, such as water or an alcohol for example, methanol, ethanol or the like, by using an inorganic basic compound such as sodium hydroxide, potassium hydroxide or the like, or an acid such as hydrochloric acid, hydrobromic acid or the like.

Next, the reaction of thus obtained compound of the general formula (10) with a compound of the general formula (11) can be carried out according to the type of a compound of the general formula (11), specifically, the type of a group of the formula $X^3$ in the compound of the general formula (11) as follows:

In a compound of the general formula (11), the examples of a halogen atom as indicated by the symbol $X^3$ including chlorine, bromine or iodine atom, the examples of a lower alkanesulfonyloxy group as indicated by the symbol $X^3$ including methanesulfonyloxy, ethanesulfonyloxy, isopropanesulfonyloxy, propanesulfonyloxy, butanesulfonyloxy, tert-butanesulfonyloxy, pentanesulfonyloxy, hexanesulfonyloxy or the like, the examples of an aralkylsulfonyloxy group as indicated by the symbol $X^3$ including a substituted or unsubstituted aralkylsulfonyloxy group, such as benzylsulfonyloxy, 2-phenylethylsulfonyloxy, 4-methylbenzylsulfonyloxy, 2-methylbenzylsulfonyloxy, 4-nitrobenzylsulfonyloxy, 4-methoxybenzylsulfonyloxy, 3-chlorobenzylsulfonyloxy, α-naphthylmethylsulfonyloxy or the like.

Among the compounds represented by the general formula (11), when a compound having a halogen atom, a lower alkanesulfonyloxy group or an aralkylsulfonyloxy group as the symbol $X^3$, the reaction of a compound of the general formula (10) with a compound of the general formula (11) can generally be carried out in a suitable inert solvent, in the presence of or absence of a basic condensing agent. As to the inert solvent used in this reaction, an aromatic hydrocarbon such as benzene, toluene, xylene or the like, a lower alcohol such as methanol, ethanol, isopropanol, butanol or the like, further acetic acid, dimethyl sulfoxide, dimethylformamide, hexamethylphosphoric triamide or the like can be exemplified. As to the basic condensing agent used in this reaction, a carbonate such as sodium carbonate, potassium carbonate, sodium bicarbonate, potassium bicarbonate or the like, metal hydroxide such as sodium hydroxide, potassium hydroxide or the like, a metal alcoholate such as sodium methylate, sodium ethylate or the like, a tertiary amine such as pyridine, triethylamine or the like can be exemplified. The ratio of the amount of a compound of the general formula (10) to the amount of a compound of the general formula (11), there is not any specific restriction and can be selected from a wide range, generally, at least an equimolar quantity, preferably an equimolar to 5 times the molar quantity of the latter may be used to the former. The reaction can be carried out at a temperature of about 40° to 120° C., preferably at about 50° to 100° C., and generally, the reaction can be completed within about 5 to 30 hours.

Among the compounds represented by the general formula (11), when a compound having a hydroxy group as the symbol $X^3$ is used, the reaction of a compound of the general formula (10) with a compound of the general formula (11) can generally be carried out in the presence of a dehydrating agent, in the absence or presence of a suitable solvent. As to the dehydrating agent used in the reaction, a condensed phosphoric acid such as polyphosphoric acid or the like, a phosphoric acid such as orthophosphoric acid, pyrophosphoric acid, metaphosphoric acid or the like, a phosphorous acid such as orthophosphorous acid, or the like, an anhydrous phosphoric acid such as phosphorous pentoxide or the like, an acid such as hydrochloric acid, sulfuric acid, boric acid or the like, a metal phosphate such as sodium phosphate, boron phosphate, ferric phosphate, aluminium phosphate or the like, further activated alumina, sodium bisulfate, Raney-nickel or the like can be exemplified. As to the solvent used in this reaction, a solvent having high boiling point such as dimethylformamide, tetrahydronaphthalene or the like can be exemplified. The ratio of the amount of a compound of the general formula (10) to the amount of a compound of the general formula (11) is not specifically restricted and can be selected from a wide range, generally, at least an equimolar quantity, preferably an equimolar to 2 times the molar quantity of the latter may be used to the former. The used amount of the dehydrating agent is not specifically restricted and can be selected from a wide range, generally at least a catalytic amount, preferably 0.5 to 5 times the molar quantity of the dehydrating agent may be used to the compound of the general formula (10). The above-mentioned reaction is carried out preferably in an inert gas stream such as in an stream of carbon dioxide or nitrogen gas for the purpose of to avoid an oxidation reaction. The reaction can be carried out either condition of a normal pressure or a pressurized condition, and preferably can be carried out under a normal condition. The reaction temperature is generally from 100° to 350° C., preferably 125° to 255° C., and the reaction can generally be completed within 3 to 10 hours. In the above-mentioned reaction, a compound of the general formula (11) may be used in the form of a salt.

REACTION PROCESS FORMULA-5

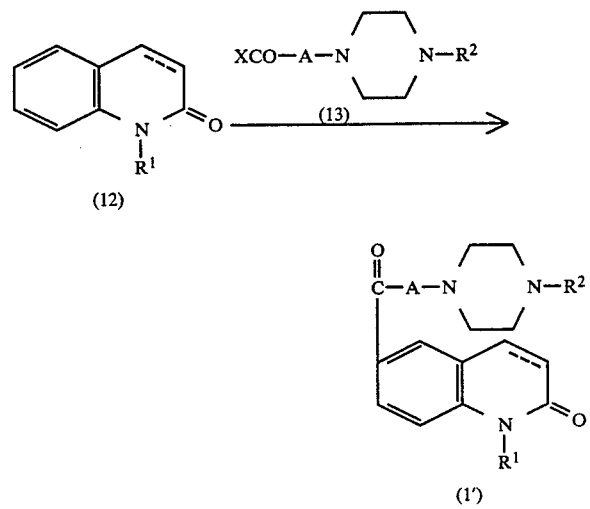

wherein $R^1$, $R^2$, A, X and the carbon-carbon bond between 3- and 4-position of the carbostyril skeleton are the same as defined above.

The reaction of a carbostyril derivative of the general formula (12) with a compound of the general formula (13) is generally called as Friedel-Craft reaction and can be carried out in the presence of a Lewis acid. This reaction can be carried out in a suitable solvent usually used in this type of the reaction, and carbon disulfide, nitrobenzene, chlorobenzene, dichloromethane, dichloroethane, trichloroethane, tetrachloroethane or the like can be used. As to the Lewis acid, any one which can be used in this type of this reaction can also be used preferably, for example aluminium chloride, zinc chloride, ferric chloride, tin chloride, boron tribromide, boron trifluoride, concentrated sulfuric acid or the like can be used. The amount of Lewis acid to be used in this reaction may be selected optionally, and generally 2 to 6 times, preferably 2 to 4 times the molar quantity of the Lewis acid may be used to the carbostyril derivative of the general formula (12). The amount of a compound of the general formula (13) the amount of the carbostyril derivative of the general formula (12) is generally at least an equimolar, preferably an equimolar to 2 times the molar quantity of a compound of the general formula (13) may be used to a compound of the general formula (12).

The reaction temperature may be selected from optionally, and generally is selected from 0° to 120° C., preferably from about 0° to 70° C. The reaction time is depend on the type of the starting materials, catalyst, reaction temperature and other factors used in the reaction, and generally the reaction may be completed within about 0.5 to 6 hours.

REACTION PROCESS FORMULA-6

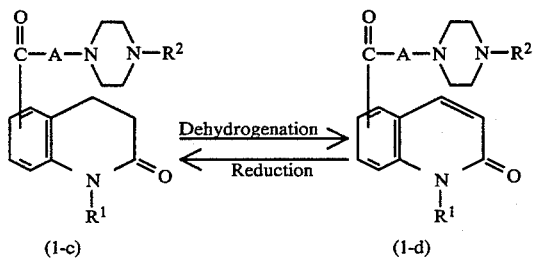

wherein $R^1$, $R^2$ A and the substituted position of the side-chain are the same as defined above.

In carrying out the reduction of a compound of the general formula (1-d), a common catalytic reduction condition may be applied. As to the catalyst used in this reduction, palladium, palladium-carbon, platinum, Raney-nickel or the like can be exemplified, and said catalyst may be used in a common catalytic amount. As to the solvent used in this reduction, methanol, ethanol, isopropanol, dioxane, tetrahydrofuran, hexane, cyclohexane, ethyl acetate or the like can be exemplified. Said reduction can be carried out either under a normal pressure or a pressurized condition, and generally at a normal pressure to 20 kg/cm$^2$, preferably at a normal pressure to 10 kg/cm$^2$. The reaction temperature is generally at 0° to 150° C., preferably at a room temperature to 100° C.

The dehydrogenation of a compound of the general formula (1-c), is carried out in a solvent with an oxidizing agent. As to the oxidizing agent, a benzoquinone such as 2,3-dichloro-5,6-dicyanobenzoquinone, chloranil 2,3,5,6-tetrachlorobenzoquinone or the like, a halogenating agent such as N-bromosuccinic imide, N-chlorosuccinic imide, bromine or the like, a hydrogenating catalyst such as selen dioxide, palladium-carbon, palladium black palladium oxide, Raney-nickel or the like can be exemplified. The amount of the oxidizing agent used in this reaction is not specifically restricted and can be selected from a wide range, and generally 1 to 5 times the molar quantity, preferably 1 to 2 times of the oxidizing agent may be used to the amount of the compound of the general formula (1-c). Further, when using the hydrogenating catalyst, a common catalytic amount of the catalyst may be used. As to the solvent used in this reaction, an ether such as dioxane, tetrahydrofuran, methoxyethanol, dimethoxyethanol or the like, an aromatic hydrocarbon such as benzene, toluene, xylene, cumene or the like, halogenated hydrocarbon such as dichloromethane, dichloroethane, chloroform, carbon tetrachloride or the like, an alcohol such as butanol, amylalcohol, hexanol or the like, a polar protic solvent such as acetic acid, an aprotic polar solvent such as dimethylformaide, dimethyl sulfoxide, hexamethylphosphoric triamide or the like can be exemplified. The reaction can generally be carried out at a room temperature to 300° C., preferably at a room temperature to 200° C., and generally, the reaction is completed within 1 to 40 hours.

Among a compounds represented by the general formula (1) of the present invention, a compound having a hydrogen atom as to the symbol $R^1$ and the carbon-carbon bond between 3- and 4-positions in the carbostyril skeleton is a double bond may be capable of exisiting in tautomeric system in the form of lactam-lactim as shown in the following reaction process formula-7.

REACTION PROCESS FORMULA-7

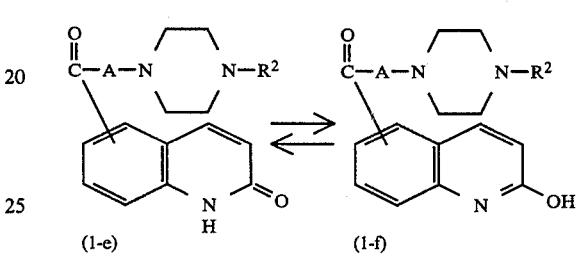

wherein $R^2$, A and the substituted position of the side-chain are the same as defied above.

REACTION PROCESS FORMULA-8

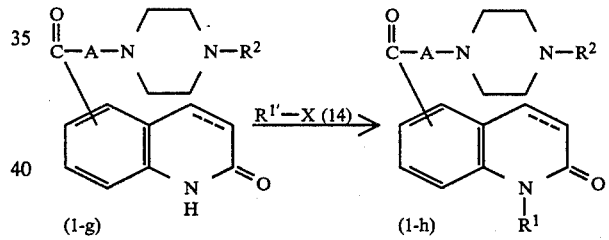

wherein $R^2$, A, X, the carbon-carbon bond between 3- and 4-positions in the carbostyril skeleton and the substituted position of the side-chain are the same as defined above; and $R^{1\prime}$ has the same meaning as defined in $R^1$ except that excluding a hydrogen atom.

The reaction of a compound of the general formula (1-g) with a compound of the general formula (14) can be carried out in a suitable solvent in the presence of a basic compound. As to the basic compound used in this reaction, sodium hydride, potassium, sodium, sodium amide, potassium amide or the like can be exemplified. As to the solvent, an ether such as dioxane, diethylene glycol dimethyl ether or the like, an aromatic hydrocarbon such as toluene, xylene or the like, further dimethylformamide, dimethyl sulfoxide, hexamethylphosphoric triamide or the like can be exemplified. The ratio of the amount of a compound of the general formula (1-g) to the amount of a compound of the general formula (14) is not specifically resticted and can be selected from a wide range, generally at least an equimolar quantity, preferably an equimolar to 2 times the molar quantity of the latter may be used to the former. The reacrtion can generally be carried out at 0° to 70° C., preferably at 0° C. to a room temperature, and generally the reaction is completed for about 0.5 to 12 hours.

Furthermore, among the compounds of the general formula (1) of the present invention, a compound having an amino group as the substituent on the phenyl ring can easily be prepared by reducing a corresponding compound which has a nitro group as the substitutent on the phenyl ring. Said reduction can be carried out under a condition commonly used in a reduction of a nitro group in aromatic compound to the corresponding amino group. More specifically, a method using sodium sulfite, sulfur dioxide or the like as the reducing agent, or a method using palladium-carbon or the like as the reducing catalyst can be applied.

A compound of the general formula (2) used as the starting material in the reaction process formula-1 including known compounds as disclosed in German Pat. No. 3,107,601 or novel compounds, and they can be prepared by a method shown in the following reaction process formula-9:

REACTION PROCESS FORMULA-9

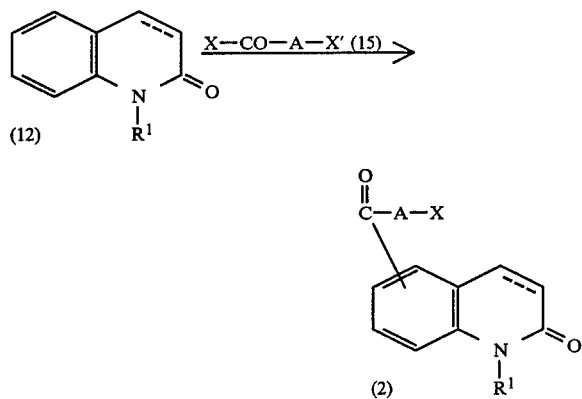

wherein $R^1$, A, X, and the substituted position of the side-chain and the carbon-carbon bond between 3- and 4-positions in the carbostyril skeleton are the same as defined above; and X' is a halogen atom.

The reaction of a compound of the general formula (12) with a compound of the general formula (15) can be carried out under a condition similar to that of the reaction of a compound of the general formula (12) with a compound of the general formula (13).

A carbostyril derivative represented by the general formula (1) of the present invention can easily be converted into an acid addition salt thereof by reacting with a pharmaceutically acceptable acid. The specified examples of the acid including an inorganic acid such as hydrochloric acid, sulfuric acid, phsophoric acid, hydrobromic acid or the like, an organic acid such as oxalic acid, maleic acid, fumaric acid, malic acid, tartaric acid, citric acid, benzoic acid and the like.

The objective compounds as prepared by the procedures in the respective reaction process formulas as mentioned above can easily be isolated and purified by conventional separation means such as a solvent extraction method, a dilution method, a recrystallization method, a column chromatography method, a preparative thin-layer chromatography method or the like.

Carbostyril derivatives of the present invention also including their optical isomers.

A carbostyril derivative represented by the general formula (1) of the present invention or a salt thereof can generally be used in the form of a pharmaceutical composition. Such pharmaceutical composition can be prepared by using diluents or excipients such as fillers, diluents, binders, wetting agents, disintegrators, surface active agents, lubricants. The pharmaceutical composition can be selected in any desired unit form, including tablets, pills, powders, liquors, suspensions, emulsions, granules, capsules, suppositories, injections (solutions and suspensions). For the purpose of to shape in the form of tablets, carriers which are known in this field can be used, for example excipients such as lactose, sucrose, sodium chloride, glucose, urea, starch, calcium carbonate, caolin, crystalin cellulose, silicic acid or the like; binding agents such as water, ethanol, propanol, simple syrup, a solution of glucose, a solution of starch, a solution of geletin, carboxymethylcellulose, shelac, methylcellulose, calcium phosphate or polyvinylpyrrolidone or the like; disintegrators such as dried starch, sodium alginate, agar-agar, powder, laminalia powder, sodium bicarbonate, calcium carbonate, esters of polyoxyethylene sorbitan fatty acids, sodium laurylsulfate, monoglyceride of stearic acid, starch, lactose or the like; desintegration inhibitors such as sucrose, stearin, coconut butter, hydrogenated oil or the like; adsorption accelerators such as a quaternary ammonium base, sodium laurylsulfate or the like; wetting agents such as glycerin, starch or the like; adsorbing agents such as starch, lactose, caolin, bentonite, colloidal silicic acid or the like; lubricants such as purified talc, stearic acid salt, boric acid powder, polyethylene glycol or the like. In case of preparing tablets, they can be further coated with an usual coating material to make them as sugar coated tablets, gelatin film coated tablets, tablets coated with enteric coatings, tablets coated with films or double-layered tablets and multi-layered tablets. For the purpose of to shape in the form of pills, carriers which are known and used widely in this fiel can also be used, such as excipients for example glucose, lactose, starch, coconut butter, hydrogeneted vegetable oil, caolin talc or the like; binders such as gum arabic powder, tragacanth gum powder, gelatin, ethanol or the like; desintegrators such as laminaria, agar-agar or the like are included. For the purpose of to shape in the form of suppositories, carriers which are known and used widely in this field can be used, for example, polyethylene glycols, coconut butter, higher alcohols, esters of higher alcohols, gelatin, semisynthesized glycerides or the like are included. For the purpose of to make in the form of injection preparations, solutions and suspensions are sterilized and are preferably isotonic to the blood. In making injection preparations, any carriers which are commonly used in this fiels can also be used, for example, water, ethyl alcohol, propylene glycol, ethoxylated isostearyl alcohol, polyoxylated isostearyl alcohol, polyoxyethylene sorbitan fatty acid esters or the like are included. In these instances, adequate amounts of sodium chloride, glucose or glycerin can be added to contain in the desired cardiotonic preparations for the purpose of to have them isotonic solution. Furthermore, usual dissolving agents, buffer solutions, analgesic agents can be added, as well as coloring agents, perfumes, preservitives, seasoning agents, sweetening agents and other medicaments can be added into the desired pharmaceutical preparation, if necessary.

The amount of a compound of the general formula (1) to be contained in the cardiotonic preparations of the present invention is not specifically restricted and it can easily be selected from a wide range, and generally 1 to 70% by weight, preferably 1 to 30% by weight of the whole composition may be used.

The cardiotonic composition of the present invention can be administered in various forms depending on the purpose without any restriction, thus the cardiotonic composition is administered in a suitable method according to the forms of the preparation, the age of the pstiant, the distinction of sex, the conditions of the symptoms and other factors. For example, tablets, pills, solutions, suspensions, emulsions, granules, and capsules are administered orally; and injection preparations are administered intraveneously singly or are mixed with injection transfusions such as glucose solutions and amino acids solutions; if necessary the injection preparations are administered singly intramuscularly, intracutaneously, subcutaneously or intraperitoneally; suppositories are administered into rectum.

The administraton dosage of a cardiotonic composition of the present invention is suitably selected according to the usage, the age of the patient, the distinction of sex, the condition of the symptoms and other factors, generally 0.01 to 10 mg/kg of the body weight per day of a compound of the general formula (1) as the active ingredient may be administered, and 0.1 to 200 mg of the active ingredient may be contained in the administration unit form.

The present invention will be illustrated more specifically by way of the following examples, in which preparation of the compounds to be used as the starting materials will be shown in Reference Examples, and preparation of the objective compounds will be shown in Examples.

REFERENCE EXAMPLE 1

In to a mixture of 200 g of 3,4-dihydrocarbostyril, 160 ml of chloroacetylchloride and 300 ml of carbon disulfide, which was ice-cooled and stirred, 460 g of anhydrous pulverized aluminium chloride was added slowly at a temperature of the reaction vessel being kept within the range of from 5° to 15° C. After the addition of aluminium chloride was completed, the reaction mixture was refluxed for 40 minutes under stirring. The carbon disulfide was removed by decantation, then the residue obtained was poured into a large amount of ice-water and the crystals thus formed was collected by filtration, and washed with water well. The crystals was washed with methanol, dried then 280 g of 6-(2-chloroacetyl)-3,4-dihydrocarbostyril was obtained. Recrystallized from ethanol to obtain a colorless needle-like crystals. Melting point: 230°–231° C.

REFERENCE EXAMPLE 2

In to a solution consisting of 6.7 g of 6-(α-chloroacetyl)-3,4-dihydrocarbostyril and 60 ml of anhydrous dimethylformamide was added 4.4 g of piperazine and 5 ml of triethylamine and the reaction mixture was stirred at 50° to 60° C. for 1 hour. The reaction mixture thus obtained was poured into a large amount of water and was extracted with chloroform. The chloroform layer was washed with water, dried and chloroform was removed by distillation. The residue obtained was suspended in a mixture of methanol-chloroform and by adding hydrochloric acid/methanol to obtain 3.5 g of 6-(1-piperazinyl)acetyl-3,4-dihydrocarbostyril monohydrochloride trihydrate in the form of colorless needle-like crystals. Melting point: 265°–267° C. (decomposed).

REFERENCE EXAMPLE 3

In to a suspension of 3.0 g of 6-chloroacetyl-3,4-dihydrocarbostyril being suspended in 20 ml of dimethylformamide was added dropwise gradually a solution consisting of 1.9 g of hexamine and 20 ml of dimethylformamide. After the addition was completed the reaction mixture was stirred at 50° to 60° C. for 2 hours. Then the crystals precipitated in the reaction mixture were collected by filtration, and were washed with methanol, dried to obtain 3.5 g of crude crystals of 6-hexaminiumacetyl-3,4-dihydrocarbostyril chloride. Then, 15 ml of ethanol and 6 ml of concentrated hydrochloric acid were added to the 3.5 g of the crude crystals of 6-hexaminiumacetyl-3,4-dihydrocarbostyril chloride and the mixture was stirred at a room temperature for 12 hours. The crystals thus formed were collected by filtration, and recrystallized from methanol-water to obtain 1.2 g of 6-aminoacetyl-3,4-dihydrocarbostyril monohydrochloride in the form of colorless powdery crystals. Melting point: Higher than 300° C.

REFERENCE EXAMPLE 4

40 Grams of 6-(α-chloroacetyl)-3,4-dihydrocarbostyril and 69 g of anhydrous piperazine were suspended in 800 ml of acetonitrile and the reaction mixture was stirred at a room temperature for 3 hours. Then the crystals precipitated in the reaction mixture were collected by filtration, and were washed with methanol, dried to obtain 40 g of crude crystals of 6-(1-piperazinyl)acetyl-3,4-dihydrocarbostyril.

The thus obtained crystals were suspended in methanol and were changed to hydrochloride by adding hydrochloric acid/methanol, and the solvent was removed by distillation, the residue thus obtained was recrystallized from water to obtain 25 g of 6-(1-piperazinyl)acetyl-3,4-dihydrocarbostyril monohydrochloride trihydrate in the form of colorless needle-like crystals. Melting point: 265°–267° C. (decomposed).

EXAMPLE 1

In to a solution consisting of 6.7 of 6-(α-chloroacetyl)-3,4-dihydrocarbostyril and 60 ml of anhydrous dimethylformamide was added 14.3 g of 4-(3,4,5-trimethoxybenzoyl)piperazine and 5 ml of triethylamine and the reaction mixture was stirred at 50° to 60° C. for 1 hour. Then the reaction mixture was poured into a large amount of water, and the organic layer was extracted with chloroform. The chloroform layer was washed with water, dried and chloroform was removed by distillation. The residue thus obtained was crystallized with ethanol and the crystals were collected by filtration, and the crystals were suspended in chloroform-methanol then were changed to hydrochloride by adding hydrochloric acid/methanol and recrystallized from ethanol to obtain 6.3 g of 6-[4-(3,4,5-trimethoxybenzoyl)-1-piperazinylacetyl]-3,4-dihydrocarbostyril monohydrochloride 3/2-hydrate in the form of colorless needle-like crystals. Melting point: 213°–217° C. (decomposed).

By a method similar to that described in Example 1, by using suitable starting materials there were prepared compounds of Examples 2 to 24 as shown in Table 1 below.

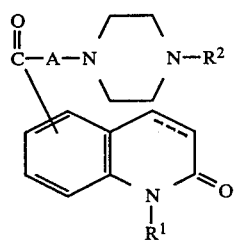

TABLE 1

| Example No. | —A— | $R^1$ | $R^2$ | 3,4 Positions in the carbostyril skeleton | Substituted position of the side-chain | Crystal form | Melting point (°C.) | Salt type |
|---|---|---|---|---|---|---|---|---|
| 2 | —CH$_2$— | H | —CO—⟨⟩—OCH$_3$ | Single bond | 6 | Colorless powdery crystals | 225–228 | 1-HCl. 1-H$_2$O |
| 3 | —CH$_2$— | H | —CO—⟨⟩—CN | Single bond | 6 | Colorless granular crystals | 254–258 | ½-H$_2$O |
| 4 | —CH$_2$— | H | —CO—⟨⟩—CH$_3$ | Single bond | 6 | Colorless powdery crystals | 242–244 | 1-HCl. 1-H$_2$O |
| 5 | —CH$_2$— | H | —CO—⟨⟩(O-CH$_2$-O) | Single bond | 6 | Colorless powdery crystals | 207–210 | 1-HCl. 1-H$_2$O |
| 6 | —CH$_2$— | H | —CO—⟨⟩—Cl, Cl | Single bond | 6 | Colorless powdery crystals | 227.5–229 (decomp) | 1-HCl. ½-H$_2$O |
| 7 | —CH$_2$— | H | —CO—⟨⟩—NO$_2$ | Single bond | 6 | Colorless granular crystals | 242–245 (decomp) | 1-HCl |
| 8 | —CH$_2$— | H | —CO—⟨furan⟩ | Single bond | 6 | Colorless needle-like crystals | 252–255 (decomp) | 1-HCl |
| 9 | —CH$_2$— | H | —CHO | Single bond | 6 | Colorless powdery crystals | 167.5–169 | — |
| 10 | —CH$_2$— | H | —COOC$_2$H$_5$ | Single bond | 6 | Colorless needle-like crystals | 235–237 (decomp) | 1-HCl. 1-H$_2$O |
| 11 | —CH$_2$— | H | —COCH$_3$ | Single bond | 6 | Colorless powdery crystals | 249–252 (decomp) | 1-HCl. ½-H$_2$O |
| 12 | —CH$_2$— | H | —COCH$_2$CH$_3$ | Single bond | 6 | Colorless needle-like crystals | 226–228 (decomp) | 1-HCl |
| 13 | —CH$_2$— | H | —SO$_2$CH$_3$ | Single | 6 | Colorless | 191–194 | 1-HCl. |

TABLE 1-continued $$O=C-A-N\underset{\phantom{x}}{\overbrace{\phantom{xxxx}}}N-R^2$$

(attached to carbostyril with N-R¹, 2-oxo)

| Example No. | —A— | R¹ | R² | 3,4 Positions in the carbostyril skeleton | Substituted position of the side-chain | Crystal form | Melting point (°C.) | Salt type |
|---|---|---|---|---|---|---|---|---|
| | | | | bond | | powdery crystals | (decomp) | 3/2-H₂O |
| 14 | —CH₂— | H | —SO₂—C₆H₄—CH₃ | Single bond | 6 | Colorless powdery crystals | 254–256 (decomp) | — |
| 15 | —CH₂— | H | —CO—C₆H₅ | Single bond | 6 | Colorless granular crystals | 207–210 | ¼-H₂O |
| 16 | —CH₂— | H | —CO—C₆H₄—Cl | Single bond | 6 | Colorless powdery crystals | 231–234 | ½-H₂O |
| 17 | —CH₂— | H | —CO—C₆H₃(OCH₃)₂ | Single bond | 6 | Colorless powdery crystals | 186–188 | — |
| 18 | —CH₂— | H | —COCH=CH—C₆H₂(OCH₃)₃ | Single bond | 6 | Colorless powdery crystals | 239–242 (decomp) | 1-HCl. 2-H₂O |
| 19 | —CH₂— | H | —COCH=CH—C₆H₄—OCH₃ | Single bond | 6 | Colorless needle like crystals | 262–264 (decomp) | 1-HCl. 1-H₂O |
| 20 | —CH₂— | H | —COCH=CH—C₆H₅ | Single bond | 6 | Colorless prism-like crystals | 270–272 (decomp) | 1-HCl. ½-H₂O |
| 21 | —CH₂— | H | —CO—C₆H₄—OCH₃ (ortho) | Single bond | 6 | Colorless powdery crystals | 250–253.5 (decomp) | 1-HCl. 1-H₂O |
| 22 | —CH₂— | H | —CH₂CH₂O—C₆H₅ | Single bond | 6 | Colorless granular crystals | 240–242 (decomp) | 2-HCl. |
| 23 | —(CH₂)₂ | H | —CO—C₆H₃(OCH₃)₂ | Single bond | 6 | Colorless needle-like crystals | 214–216 (decomp) | 1-HCl |
| 24 | —CH— CH₃ | H | —CO—C₆H₃(OCH₃)₂ | Single bond | 6 | Colorless powdery crystals | 229–233 (decomp) | 1-HCl. |

EXAMPLE 25

Two grams of 6-(1-piperazinyl)acetyl-3,4-dihydrocarbostyril and 1.4 ml of triethylamine were dissolved in 20 ml of dimethylformamide. Into this solution was added a solution consisting of 2.2 g of 3,4,5-trimethoxybenzoyl chloride and 5 ml of dimethylformamide dropwise gradually at a room temperature under stirring condition. The reaction mixture was stirred at a room temperature for additional 30 minutes, then the reaction mixture was poured into a large amount of a saturated sodium chloride aqueous solution and extracted with chloroform. The chlorofom layer was washed with water and then dried with anhydrous sodium sulfate, and chloroform was removed by distillation. The residue thus obtained was crystallized with ethanol and the crystals formed were collected by filtration. The crystals were suspended in a mixed solvent of methanol/chloroform, then were changed to hydrochloride by adding hydrochloric acid/ethanol. The solvent was removed by distillation and the residue thus obtained was crystallized by adding ethanol. Recrystallized from ethanol to obtain 1.2 g of 6-[4-(3,4,5-trimethoxybenzoyl)-1-piperazinylacetyl]-3,4-dihydrocarbostyril monohydrochloride 3/2-hydrate in the form of colorless needle-like crystals. Melting point: 213°–217° C. (decomposed).

By a method similar to that described in Example 25, by using suitable starting materials, there were obtained compounds of the above-mentioned Examples 2–12, 15–21, 23 and 24 respectively.

EXAMPLE 26

1.6 Grams of 6-(1-piperazinylacetyl)-3,4-dihydrocarbostyril and 1.5 -g of triethylamine were suspended in 10 ml of dichloromethane, and into this suspension was added a solution of 1.4 g of p-toluenesulfonyl chloride in 10 ml of dichloromethane dropwise under ice-cooling condition with stirring. Then the reaction mixture was stirred for additional 3 hours at a room temperature and further stirred under ice-cooled condition for 1 hour. The crystals formed in the reaction mixture were collected by filtration, recrystallized from chloroform-ether to obtain 0.4 g of 6-[4-(p-toluenesulfonyl)-1-piperazinylacetyl]-3,4-dihydrocarbostyril in the form of colorless powdery crystals. Melting point: 254°–256° C. (decomposed).

By a method similar to that described in Example 26, by using suitable starting materials, there were obtained compounds of the above-mentioned Examples 13 and 22 respectively.

EXAMPLE 27

A mixture of 5.0 g of 6-(α-aminoacetyl)-3,4-dihydrocarbostyril, 10.8 g of (3,4,5-trimethoxybenzoyl)-[di-(2-hydroxyethyl)]amine and 7.6 g of polyphosphoric acid was reacted at 160°–170° C. for about 6 hours. Then the reaction mixture was cooled to a room temperature and dissolved by adding about 500 ml of water. The solution was then neutralized with 48%-sodium hydroxide aqueous solution and extracted with chloroform. The chloroform layer was dried with anhydrous potassium carbonate, then chloroform was removed by distillation. The residue thus obtained was changed to hydrochloride by adding concentrated hydrochloric acid/ethanol, and recrystallized from ethanol to obtain 1.5 g of 6-[4-(3,4,5-trimethoxybenzoyl)-1-piperazinylacetyl]-3,4-dihydrocarbostyril monohydrochloride 3/2-hydrate in the form of colorless needle-like crystals. Melting point: 213°–217° C. (decomposed).

By a method similar to that described in Example 27, by using suitable starting materials, there were obtained compounds of Examples 2–24.

EXAMPLE 28

A mixture of 11.9 g of 6-(α-aminoacetyl)-3,4-dihydrocarbostyril, 17.0 g of 3,4,5-trimethoxybenzoyl-[bis(2-chloroethyl)]amine and 70 ml of methanol was refluxed for 15 hours under stirring condition. After cooling the reaction mixture, 3.06 g of sodium carbonate was added thereto and the whole mixture was refluxed with stirring for 8 hours. The reaction mixture was allowed to stand for cooling and the precipitated crystals were collected by filtration. Then the disired product thus obtained was changed to a hydrochloride by adding a concentrated hydrochloric acid/ethanol, and recrystallized from ethanol to obtain 7.3 g of 6-[4-(3,4,5-trimethoxybenzoyl)-1-piperazinylacetyl]-3,4-dihydrocarbostyril monohydrochloride 3/2-hydrate in the form of colorless needle-like crystals. Melting point: 213°–217° C. (decomposed).

By a method similar to that described in Example 28, there were prepared compounds of the above-mentioned Examples 2–24.

EXAMPLE 29

Into 100 ml of dimethylformamide was added 3.6 g of 3,4,5-trimethoxybenzoic acid and 1.65 g of 1,8-diazabicyclo-[5,4,0]undecene-7, and outside of the reaction vessel containing the above-mentioned mixture was ice-cooled, then 1.5 ml of isobutyl chloroformate was added dropwise into the reaction mixture under stirring condition. After the addition was finished, the reaction mixture was further stirred for 30 minutes additionally, then a mixture prepared by dissolving 2.27 g of 6-(1-piperazinylacetyl)-3,4-dihydrocarbostyril in 40 ml of dimethylformamide was added to the reaction mixture and the whole reaction mixture was stirred at a room temperature for 5 hours. After the reaction was completed, the solvent was removed by distillation and the residue obtained was extracted with 300 ml of chloroform, then the chloroform layer was washed with a diluted sodium bicarbonate aqueous solution, water, a diluted hydrochloric acid and water. Chloroform was removed by distillation, and the residue obtained was changed to a hydrochloride by adding hydrochloric acid/ethanol. Recrystallized from ethanol to obtain 2.1 g of 6-[4-(3,4,5-trimethoxybenzoyl)-1-piperazinylacetyl]-3,4-dihydrocarbostyril monohydrochloride 3/2-hydrate in the form of colorless needle-like crystals. Melting point: 213°–217° C. (decomposed).

By a method similar to that described in Example 29, by using suitable starting materials there were prepared compounds of the above-mentioned Examples 2–24.

EXAMPLE 30

Into a mixed solvent of 20 ml of dioxane and 20 ml of methylene chloride was added 2.76 g of 6-(1-piperazinylacetyl)-3,4-dihydrocarbostyril and 2.25 g of 3,4,5-trimethoxybenzoic acid. Then, into this mixture was added dropwise a solution of 2.1 g of N,N'-dicyclohexylcarbodiimide dissolved in 5 ml of methylene chloride under a condition in which the reaction vessel was iced-cooled with stirring. After the addition was finished, the reaction mixture was stirred for additional 3.5 hours at the same temperature. The crystals thus formed in the reaction mixture were removed by filtration, and the filtrate thus obtained was concentrated to dryness under a reduced pressure. The residue thus obtained was dissolved in 100 ml of methylene chloride and the organic layer was washed with water, then the organic layer was dried with anhydrous sodium sulfate. The solvent was removed by distillation under a reduced pressure, then the residue obtained was changed to a hydrochloride by adding hydrochloric acid/methanol. Recrystallized from ethanol to obtain 0.8 g of 6-[4-(3,4,5-trimethoxybenzoyl)-1-piperazinylacetyl]-3,4-dihydrocarbostyril monohydrochloride 3/2-hydrate in the form of colorless needle-like crystals. Melting point: 213°–217° C. (decomposed).

By a method similar to that described in Example 30, by using suitable starting materials, there were prepared compounds of the above-mentioned Examples 2–12, 15–21, 23 and 24.

EXAMPLE 31

136 Milligrams of succinyl imide 3,4,5-trimethoxybenzoate and 144 mg of 6-(1-piperazinylacetyl)-3,4-dihydrocarbostyril were dissolved in 2 ml of dimethylformamide and the mixture was stirred for 24 hours. Then, water was added to the reaction mixture, and was extracted with chloroform. The chloroform layer was washed with water and a saturated aqueous solution of sodium chloride, then the chloroform solution was dried with anhydrous sodium sulfate, the solvent was removed by distillation under a reduced pressure and the residue obtained was changed to a hydrochloride by adding hydrochloric acid/methanol. Recrystallized from ethanol to obtain 110 mg of 6-[4-(3,4,5-trimethoxybenzoyl)-1-piperazinylacetyl]-3,4-dihydrocarbostyril monohydrochloride 3/2-hydrate. Melting point: 213°–217° C. (decomposed).

By a method similar to that described in Example 31, by using suitable starting materials, there were prepared compounds of the above-mentioned Examples 2–12, 15–21, 23 and 24.

EXAMPLE 32

Into 100 ml of ethanol was added 2.19 g of ethyl 3,4,5-trimethoxybenzoate, 0.5 g of sodium ethylate and 2.48 g of 6-(1-piperazinylacetyl)-3,4-dihydrocarbostyril, and the mixture obtained was placed in an autoclave, and the reaction was carried out at 110 atmospheric pressure at 140°–150° C. for 6 hours. After the reaction mixture was cooled to a room temperature, the reaction mixture was concentrated under a reduced pressure and the residue obtained was dissolved in 200 ml of chloroform, then washed with 1%-potassium carbonate aqueous solution, a diluted hydrochloric acid and water in this order. Then the chloroform extract was dried with anhydrous sodium sulfate, and chloroform was removed by distillation. The residue obtained was purified by a silica gel column chromatography (silica gel=Wako C-200; eluent=chloroform/methanol (v/v)=20:1). To the eluate was added hydrochloric acid/methanol to change the desired product into a hydrochloride. Recrystallized from ethanol to obtain 250 mg of 6-[4-(3,4,5-trimethoxybenzoyl)-1-piperazinylacetyl]-3,4-dihydrocarbostyril monohydrochloride 3/2-hydrate in the form of colorless needle-like crystals. Melting point: 213°–217° C. (decomposed).

By a method similar to that described in Example 32, by using suitable starting materials, there were prepared compounds of the above-mentioned Examples 2–12, 15–21, 23 and 24.

EXAMPLE 33

Into a solution of 1.0 g of 6-(1-piperzinyl)-acetylcarbostyril and 0.67 ml of triethylamine in 10 ml of dimethylformamide was added dropwise gradually to a solution of 780 ml of m-chlorobenzoyl chloride in 2 ml of dimethylformamide under ice-cooled condition with stirring. After the addition was finished, the reaction mixture was further stirred for 2 hours at a room temperature. Then the reaction mixture was poured into a large amount of half-saturated sodium chloride aqueous solution and extracted with chloroform. The chloroform layer was washed with water, dried with anhydrous sodium sulfate and chloroform was removed by distillation under a reduced pressure. The residue obtained was crystallized with ether, then the crystals were collected by filtration and recrystallized from ethanol. The crystals were dissolved in methanol/chloroform and changed to hydrochloride by adding concentrated hydrochloric acid/ethanol. The solvent was removed by distillation, the residue obtained was crystallized with ethanol, and the crystals were collected by filtration, then recrystallized from methanol to obtained 370 mg of 6-[4-(3-chlorobenzoyl)-1-piperazinylacetyl]-carbostyril monohydrochloride hydrate in the form of colorless powdery crystals. Melting point: 212°–215° C. (decomposed).

By a method similar to that described in Example 33, by using suitable starting materials, there were prepared compounds of Examples 34–42 as shown in Table 2 below.

TABLE 2

$$\text{O=C-A-N}\underset{\underset{}{}}{\overset{\overset{}{}}{\diagup\diagdown}}\text{N-R}^2$$

(carbostyril skeleton with N-R$^1$ and C=O)

| Example No. | —A— | R$^1$ | R$^2$ | 3,4- Positions in the carbostyril skeleton | Substituted position of the side chain | Crystal form | Melting point (°C.) | Salt type |
|---|---|---|---|---|---|---|---|---|
| 34 | —CH$_2$— | H | 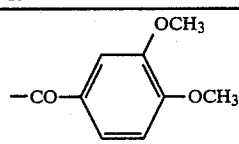 | Double bond | 6 | Colorless powdery crystals | 206–207 (decomp) | 1-HCl. |

TABLE 2-continued

O=C—A—N(piperazine)N—R²
[attached to carbostyril skeleton with N-R¹ and =O]

| Example No. | —A— | R¹ | R² | 3,4-Positions in the carbostyril skeleton | Substituted position of the side chain | Crystal form | Melting point (°C.) | Salt type |
|---|---|---|---|---|---|---|---|---|
| 35 | —CH₂— | H | —CO—(benzene)—O–CH₂–O– (methylenedioxy) | Double bond | 6 | Colorless granular crystals | 249–251 (decomp) | ½-H₂O |
| 36 | —CH₂— | H | —CO—(C₆H₄)—OCH₃ | Double bond | 6 | Colorless powdery crystals | 215–217 (decomp) | 1-HCl. |
| 37 | —CH₂— | H | —CO—(C₆H₄)—CH₃ | Double bond | 6 | Colorless powdery crystals | 216–218 (decomp) | 1-HCl. 3/2-H₂O |
| 38 | —CH₂— | H | —CO—(C₆H₅) | Double bond | 6 | Colorless powdery crystals | 212–214 (decomp) | 1-HCl. 3/2-H₂O |
| 39 | —CH₂— | H | —CO—(C₆H₄)—CN | Double bond | 6 | Colorless powdery crystals | 218–220 (decomp) | 1-HCl. 3/2-H₂O |
| 40 | —CH₂— | H | —CO—(C₆H₂)(OCH₃)₃ (3,4,5-trimethoxy) | Double bond | 6 | Colorless powdery crystals | 201–204 (decomp) | 1-HCl. 3/2-H₂O |
| 41 | —CH₂— | H | —CO—(C₆H₄)—NO₂ | Double bond | 6 | Colorless powdery crystals | 214–216 (decomp) | 1-HCl. ½-H₂O |
| 42 | —CH₂— | H | —CO—(C₆H₄)—NH₂ | Double bond | 6 | Colorless powdery crystals | Over 300 | 2-HCl. 1-H₂O |

EXAMPLE 43

Into a solution of 6.6 g of 6-(α-chloroacetyl)-carbostyril in 60 ml of anhydrous dimethylformamide was added 14.3 g of 4-(3,4,5-trimethoxybenzoyl)piperazine and 5 ml of triethylamine, and this mixture was stirred at 50° to 60° C. for 1 hour. The reaction mixture was then poured into a large amount of water, and the organic layer was extracted with chloroform. The chloroform layer was washed with water, dried and chloroform was removed by distillation. The residue thus obtained was crystallized with ethanol and the crystals formed were collected by filtration. The crystals obtained were suspended in methanol-chloroform and by adding hydrochloric acid/ethanol to change the product to a hydrochloride. Recrystallized from methanol to obtain 6.0 g of 6-[4-(3,4,5-trimethoxybenzoyl)-1-piperazinylacetyl]carbostyril monohydrochloride 3/2- hydrate in the form of colorless powdery crystals. Melting point: 201°–204° C. (decomposed).

By a method similar to that described in Example 43, by using suitable starting materials, there were prepared compounds of the above-mentioned Examples 33–39, 41 and 42.

EXAMPLE 44

A mixture of 4.9 g of 6-(α-aminoacetyl)-carbostyril, 10.8 g of (3,4,5-trimethoxybenzoyl)-[di-(2-hydroxyethyl)]amine and 7.6 g of polyphosphoric acid was reacted at 160°–170° C. for about 6 hours. After the reaction was completed, the reaction mixture was allowed to stand for cooling, then about 500 ml of water was added dropwise into the reaction mixture to dissolve it. The solution was neutralized with 48%-sodium hydroxide aqueous solution and then extracted with chloroform. The chloroform layer was dried with anhydrous potassium carbonate, and chloroform was removed by distillation. The residue thus obtained was changed to a hydrochloride by adding a concentrated hydrochloric acid/ethanol. Recrystallized from methanol to obtain 1.4 g of 6-[4-(3,4,5-trimethoxydibenzoyl)-1-piperazinylacetyl]-carbostyril monohydrochloride 3/2-hydrate in the form of colorless powdery crystals. Melting point: 201°–204° C. (decomposed).

By a method similar to that described in Example 44, by using suitable starting materials, there were prepared compounds of the above-mentioned Examples 33–39, 41 and 42.

EXAMPLE 45

A mixture of 11.8 g of 6-(α-aminoacetyl)-carbostyril, 17.0 g of 3,4,5-trimethoxybenzoyl[(bis(2-chloroethyl)]amine and 70 ml of methanol was refluxed with stirring condition for 15 hours. Next, the reaction mixture was cooled and 3.06 g of sodium carbonate was added thereto and then further refluxed with stirring condition for 8 hours. After cooled the reaction mixture, the crystals formed were collected by filtration and by adding a concentrated hydrochloric acid/ethanol to change it to a hydrochloride. Recrystallized from methanol to obtain 7.1 g of 6-[4-(3,4,5-trimethoxybenzoyl)-1-piprazinylacetyl]carbostyril monohydrochloride 3/2-hydrate in the form of colorless powdery crystals. Melting point: 201°–204° C. (decomposed).

By a method similar to that described in Example 45, by using suitable starting materials, there were prepared compounds of the above-mentioned Examples 33–39, 41 and 42.

EXAMPLE 46

Into 100 ml of dimethylformamide was added 3.6 g of 3,4,5-trimethoxybanzoic acid and 1.65 g of 1,8-diazabicyclo[5,4,0]undecene-7, then outside of reaction vessel containing the mixture was ice-cooled and 1.5 ml of isobutyl chloroformate was added dropwise thereto under stirring condition. After the addition was finished, the reaction mixture was further stirred for additional 30 minutes, then a solution of 2.25 g of 6-(1-piperazinylacetyl)carbostyril dissolved in 40 ml of dimethylformamide was added to the mixture and stirred at a room temperature for 5 hours under stirring condition. After the reaction was completed, the solvent was removed by distillation and the residue obtained was extracted with 300 ml of chloroform, and the chloroform layer was washed with a diluted sodium bicarbonate aqueous solution, water, a diluted hydrochloric acid, water in this order. Chloroform was removed by distillation, the residue obtained was changed to a hydrochloride by adding hydrochloric acid/ethanol. Recrystallized from methanol to obtain 2.0 g of 6-[4-(3,4,5-trimethoxybenzoyl)-1-piperazinylacetyl]-carbostyril monohydrochloride 3/2-hydrate in the form of colorless powdery crystals. Melting point: 201°–204° C. (decomposed).

By a method similar to that described in Example 46, by using suitable starting materials, there were prepared compounds of the above-mentioned Examples 33–39, 41 and 42.

EXAMPLE 47

Into a mixed solvent of 20 ml of dioxane with 20 ml of methylene chloride was added 27.4 g 6-(1-piperazinylacetyl)carbostyril and 2.25 g of 3,4,5-trimethoxybenzoic acid, then outside of the vessel containing the mixture was ice-cooled, and a solution of 2.1 g of N,N'-dicyclohexylcarbodiimide dissolved in 5 ml of methylene chloride was added dropwise to the mixture under stirring condition by keeping the temperature of the reaction mixture about 10°–20° C. After the addition was finished, the reaction mixture was stirred at a room temperature for additional 3.5 hours. The crystals precipitated were removed by filtration, and the filtrate obtained was concentrated under a reduced pressure to dryness. The residue obtained was dissolved in 100 ml of methylene chloride, and the organic layer was washed with 5%-hydrochloric acid aqueous solution, 5%-sodium bicarbonate aqueous solution and water in this order, then the organic layer was dried with anhydrous sodium sulfate, and the solvent was removed by distillation under a reduced pressure. The residue obtained was change to a hydrochloride by adding hydrochloric acid/ethanol. Recrystallized from methanol to obtain 0.8 g of 6-[4-(3,4,5-trimethoxybenzoyl)-1-piperazinylacetyl]carbostyril monohydrochloride 3/2-hydrate in the form of colorless powdery crystals. Melting point: 201°–204° C. (decomposed).

By a method similar to that described in Example 47, by using suitable starting materials, there were prepared compounds of the above-mentioned Examples 33–39, 41 and 42.

EXAMPLE 48

136 Milligrams of succinylimide 3,4,5-trimethoxybenzoate and 143 mg of 6-(1-piperazinylacetyl)carbostyril were dissolved in 2 ml of dimethylformamide, and the solution obtained was stirred for 24 hours. To this reaction mixture was added water and then extracted with chloroform. The chloroform layer was washed with water, a saturated sodium chloride aqueous solution, then dried with anhydrous sodium sulfate and the solvent was removed by distillation under a reduced pressure. The residue obtained was changed to a hydrochloride by adding hydrochloric acid/ethanol. Recrystallized from methanol to obtain 103 mg of 6-[4-(3,4,5-trimethoxybenzoyl)-1-piperazinylacetyl]-carbostyril monohydrochloride 3/2-hydrate in the form of colorless powdery crystals. Melting point: 201°–204° C. (decomposed).

By a method similar to that described in Example 48, by using suitable starting materials, there were prepared compounds of the above-mentioned Examples 33–39, 41 and 42.

EXAMPLE 49

Into 100 ml of ethanol was added 2.19 g of ethyl 3,4,5-trimethoxybenzoate, 0.5 g of sodium ethylate and 2.46 g of 6-(1-piperazinylacetyl)carbostyril, and the mixture was reacted in an autoclave under 110 atmospheric pressure at 140°-150° C. for 6 hours. After cooled the reaction mixture was concentrated under a reduced pressure, and the residue obtained was dissolved in 200 ml of chloroform, then the chloroform layer was washed with 1%-potassium carbonate aqueous solution, a diluted hydrochloric acid, water, in this order then was dried with anhydrous sodium sulfate, and the solvent was remove by distillation under a reduced pressure. The residue obtained was purified by a silica gel column chromatography (silica gel: Wako C-200, eluent: chloroform/methanol (v/v)=20:1), then change to a hydrochloride by adding a hydrochloric acid/ethanol. Recrystallized from methanol to obtain 232 mg of 6-[4-(3,4,5-trimethoxybenzoyl)-1-piperazinylacetyl]carbostyril monohydrochloride 3/2-hydrate in the form of colorless powdery crystals. Melting point: 201°-204° C. (decomposed).

By a method similar to that described in Example 49, by using suitable starting materials, there were prepared compounds of the above-mentioned Examples 33-39, 41 and 42.

EXAMPLE 50

Into a mixture of 20 g of 3,4-dihydrocarbostyril, 71.5 g of 4-(3,4,5-trimethoxybenzoyl)-1-piperazinylacetyl chloride and 30 ml of carbon disulfide was added gradually 46 g of pulverized anhydrous aluminum chloride by ice-cooling the outside of the reaction vessel, with stirring, at 5°-15° C. of the inside of the vessel. After the addition was finished, the reaction mixture was further refluxed with stirring for additional 40 minutes. Carbon disulfide was removed by decantation, the residue obtained was poured into a large amount of ice-water and the mixture was neutralized with sodium hydroxide then the crystals precipitated were collected by filtration, washed well with water, then further washed with methanol. After dried the crystals were suspended in methanol-chloroform and then changed to a hydrochloride by adding hydrochloric acid/methanol, recrystalized from ethanol to obtain 6.3 g of 6-[4-(3,4,5-trimethoxybenzoyl)-1-piperazinylacetyl]-3,4-dihydrocarbostyril monohydrochloride 3/2-hydrate in the form of colorless needle-like crystals. Melting point: 213°-217° C. (decomposed).

By a method similar to that described in Example 50, by using suitable starting materials, there were prepared compounds of the above-mentioned Examples 2-24.

EXAMPLE 51

Into a mixture of 19.7 g of carbostyril, 71.5 g of 4-(3,4,5-trimethoxybenzoyl)-1-piperazinylacetyl chloride and 30 ml of carbon disulfide was added gradually 46 g of pulverized anhydrous aluminum chloride by ice-cooling the outside of the reaction vessel, with stirring, at 5°-15° C. of the inside of the vessel. After the addition was finished, the reaction mixture was further refluxed with stirring for additional 40 minutes. Carbon disulfide was removed by decantation, the residue obtained was poured into a large amount of ice-water, and the mixture was neutralized with sodium hydroxide then the crystals formed were collected by filtration, washed well with water, then with methanol. After dried the crystals were suspended in methanol-chloroform and then changed to a hydrochloride by adding hydrochloric acid/ethanol. Recrystallized from methanol to obtain 6.2 g of 6-[4-(3,4,5-trimethoxybenzoyl)-1-piperazinylacetyl]carbostyril monohydrochloride 3/2-hydrate in the form of colorless powdery crystals. Melting point: 201°-204° C. (decomposed).

By a method similar to that described in Example 51, by using suitable starting materials, there were prepared compounds of the above-mentioned Examples 33-39, 41 and 42.

EXAMPLE 52

498 Milligrams of 6-[4-(2-phenoxyethyl)-1-piperazinylacetyl]-3,4-dihydrocarbostyril and 70 mg of 50%-sodium hydride in oil were admixed in 5 ml of dimethylformamide, then the mixture was stirred at a room temperature for 1 hour. Next, into this reaction mixture was added a solution of 0.17 ml of benzyl chloride in 3 ml of dimethylformamide and stirred at a room temperature for 4 hours. The reaction mixture was poured into a large amount of water and the organic layer was extracted with chloroform, then the chloroform layer was washed with water, dried and chloroform was removed by distillation. The residue obtained was changed to a hydrochloride by adding a concentrated hydrochloric acid to obtain 150 mg of 1-benzyl-6-[4-(2-phenoxyethyl)-1-piperazinylacetyl]-3,4-dihydrocarbostyril monohydrochloride in the form colorless crystals. Melting point: 230°-234° C. (decomposed).

Elemental analysis (for $C_{30}H_{33}N_3O_3 \cdot HCl$) Calculated (%): C 69.28; H 6.59; N 8.08, Found: (%): C 69.08; H 6.74; N 7.98.

EXAMPLE 53

498 Milligrams of 6-[4-(2-phenoxyethyl-1-piperazinylacetyl]-3,4-dihydrocarbostyril and 70 mg of sodium hydride in oil were admixed into 5 ml of dimethylformamide, then the mixture was stirred at a room temperature for 1 hour. Next, into this reaction mixture was added 0.23 g of methyl iodide drop wise gradually, and stirred at a room temperature for 4 hours. The reaction mixture was poured into a large amount of water and the organic layer was extracted with chloroform, then the chloroform layer was washed with water, dried and chloroform was removed by distillation. The residue obtained was changed to a hydrochloride by adding a concentrated hydrochloric acid to obtain 132 mg of 1-methyl-6-[4-(2-phenoxyethyl)-1-piperazinylacetyl]-3,4-dihydrocarbostyril monohydrochloride in the form of colorless crystals. Melting point: 115°-120° C. (decomposed).

Elemental analysis (for $C_{24}H_{29}N_3O_3 \cdot HCl$) Calculated (%): C 70.56; H 7.40; N 10.29, Found (%): C 70.41; H 7.51; N 10.09.

EXAMPLE 54

498 Milligrams of 6-[4-(2-phenoxyethyl)-1-piperazinylacetyl]-3,4-dihydrocarbostyril and 70 mg of 50%-sodium hydride in oil were admixed in 5 ml of dimethylformamide, then the mixture was stirred at a room temperature for 2 hours. Next, into this reaction mixture was added 0.17 g of propargyl chloride and stirred at a room temperature for 7 hours. The reaction mixture was poured into 13 ml of a saturated sodium chloride aqueous solution and the organic material was extracted with water, dried and chloroform was removed by distillation. The residue obtained was purified by a silica gel column chromatography and the product obtained was changed to a hydrochloride by adding a concentrated hydrochloric acid, to obtain 85 mg of 1-(2-propynyl)-6-[4-(2-phenoxyethyl)-1-piperazinylacetyl]-3,4-dihydrocarbostyril monohydrochloride in the form of colorless crystals. Melting point: 209°–211° C. (decomposed).

Elemental analysis (for $C_{26}H_{29}N_3O_3 \cdot HCl$) Calculated (%): C 66.73; H 6.46: N 8.98, Found (%) C 66.48; H 6.66; N 9.19.

EXAMPLE 55

498 Milligrams of 6-[4-(2-phenoxyethyl)-1-piprazinylacetyl]-3,4-dihydrocarbostyril and 0.05 g of sodium amide were admixed in 5 ml of dimethylformamide, then the mixture was stirred at a room temperature for 2 hours. Next into this reaction mixture was added 0.17 g of acryl chloride and stirred at a room temperature for 10 hours. The reaction mixture was poured into 13 ml of a saturated sodium chloride aqueous solution and the organic substances were extracted with chloroform, then the chloroform layer was washed with water, dried and chloroform was removed by distillation. The residue obtained was purified by a silica gel column chromatography and the product obtained was changed to a hydrochloride by adding a concentrated hydrochloric acid to obtain 91 mg of 1-allyl-6-[4-(2-phenoxyethyl)-1-piperazinylacetyl]-3,4-dihydrocarbostyril monohydrochloride in the form of colorless crystals. Melting point: 107°–110° C. (decomposed).

Elemental analysis (for $C_{26}H_{31}N_3O_3 \cdot HCl$) Calculated (%): C 66.44; H 6.86; N 8.94, Found (%): C 66.14; H 6.61; N 9.15.

EXAMPLE 56

Into a solution of 6.7 g of 8-(α-chloroacetyl)-3,4-dihydrocarbostyril in 60 ml of anhydrous dimethylformamide was added 14.3 g of 4-(3,4,5-trimethoxybenzoyl)-piperazine and 5 ml of triethylamine, then the mixture was stirred at 50°–60° C. for 1 hour. The reaction mixture was poured into a large amount of water, then the organic layer was extracted with chloroform. The chloroform layer was washed with water and dried then chloroform was removed by distillation. The residue obtained was crystallized with ethanol and the crystals were collected by filtration. The crystals were suspended in methanol-chloroform and changed to a hydrochloride by adding hydrochloric acid/methanol to obtain 4.7 g 8-[4-(3,4,5-trimethoxybenzoyl)-1-piperazinylacetyl]-3,4-dihydrocarbostyril monohydrochloride in the form of colorless crystals. Melting point: 158°–162° C.

Elemental analysis (for $C_{25}H_{29}N_3O_6 \cdot HCl$) Calculated (%): C 64.09; H 6.45; N 8.97, Found (%): C 64.26; H 6.34; N 9.09.

EXAMPLE 57

Into a solution of 6.7 g of 5-(α-chloroacetyl)-3,4-dihydrocarbostyril in 60 ml of anhydrous dimethyl formamide was added 14.3 g of 4-(3,4,5-trimethoxybenzoyl)-piperazine and 5 ml of triethylamine, then the mixture was stirred at 50°–60° C. for 1 hour. The reaction mixture was poured into a large amount of water and the organic layer was extracted with chloroform. The chloroform layer was washed with water, dried and chloroform was removed by distillation. The residue obtained was crystallized with ethanol and the crystals formed were collected by filtration. The crystals were suspended in methanol-chloroform and changed to a hydrochloride by adding hydrochloric acid/methanol to obtain 4.3 g of 5-[4-(3,4,5-trimethoxybenzoyl)-1-piperazinylacetyl]-3,4-dihydrocarbostyril monohydrochloride in the form of colorless crystals. Melting point: 157°–162° C.

Elemental analysis (for $C_{25}H_{29}N_3O_6 \cdot HCl$) Calculated (%): C 64.09; H 6.45; N 8.97, Found (%): C 64.26; H 6.34; N 9.09.

EXAMPLE 58

A mixture of 6.7 g of 6-(α-chloroacetyl)-3,4-dihydrocarbostyril, 14.3 g of 4-(3,4,5-trimethoxybenzoyl)-piperazine, 4.8 g of potassium carbonate and 60 ml of anhydrous dimethylformamide was stirred at 50° to 60° C. for 1 hour. Then the reaction mixture was poured into a large amount of water, and the organic layer was extracted with chloroform. The chloroform layer was washed with water, dried and chloroform was removed by distillation. The residue was crystallized from ethanol and the crystals were collected by filtration, then the crystals were suspended in chloroform-methanol, and were changed to hydrochloride by adding hydrochloric acid/methanol, and recrystallized from ethanol to obtain 6.5 g of 6-[4-(3,4,5-trimethoxybenzoyl)-1-piperazinylacetyll-3,4-dihydrocarbostyril monohydrochloride 3/2-hydrate in the form of colorless needle-like crystals. Melting point: 213°–217° C. (decomposed).

Pharmacological activities of compounds of the general formula (1) of the present invention were conducted by test methods as explained below with the results as follows:

COMPOUNDS USED IN THE TESTS ARE AS FOLLOWS

| Compound No. | Name of the compound |
|---|---|
| 1 | 6-[4-(4-Methylbenzoyl)-1-piperazinylacetyl]-3,4-dihydrocarbostyril monohydrochloride monohydrate |
| 2 | 6-[4-(4-Cyanobenzoyl)-1-piperazinylacetyl]-3,4-dihydrocarbostyril ½-hydrate |
| 3 | 6-[4-(4-Methoxybenzoyl)-1-piperazinylacetyl]-3,4-dihydrocarbostyril monohydrochloride monohydrate |
| 4 | 6-[4-(3,4-Methylenedioxybenzoyl)-1-piperazinylacetyl]-3,4-dihydrocarbostyril monohydrochloride monohydrate |
| 5 | 6-[4-(4-Nitrobenzoyl)-1-piperazinylacetyl]-3,4-dihydrocarbostyril monohydrochloride |
| 6 | 6-(4-Acetyl-1-piperazinylacetyl)-3,4-dihydrocarbostyril monohydrochloride ½-hydrate |
| 7 | 6-(4-Ethoxycarbonyl-1-piperazinylacetyl)-3,4-dihydrocarbostyril monohydrochloride |
| 8 | 6-(4-Methanesulfonyl-1-piperazinylacetyl)-3,4-dihydrocarbostyril monohydrochloride 3/2-hydrate |
| 9 | 6-(4-Formyl-1-piperazinylacetyl)-3,4-dihydrocarbostyril |
| 10 | 6-[4-(3,4-Dimethoxybenzoyl)-1-piperazinylacetyl]-3,4-dihydrocarbostyril |
| 11 | 6-[4-(3-Chlorobenzoyl)-1-piperazinylacetyl]-3,4-dihydrocarbostyril ½-hydrate |
| 12 | 6-[4-(3,4-Methylenedioxybenzoyl)-1-piperazinylacetyl]carbostyril ½-hydrate |
| 13 | 6-[4-(3,4-Dichlorobenzoyl)-1-piperazinylacetyl]-3,4-dihydrocarbostyril monohydrochloride ½-hydrate |
| 14 | 6-(4-Furoyl-1-piperazinylacetyl)-3,4-dihydrocarbostyril monohydrochloride |
| 15 | 6-(4-Benzoyl-1-piperazinylacetyl)-3,4- |

-continued

| Compound No. | Name of the compound |
|---|---|
|  | dihydrocarbostyril ½-hydrate |
| 16 | 6-[4-(3-Chlorobenzoyl)-1-piperazinylacetyl]-carbostyril monohydrochloride monohydrate |
| 17 | 6-[4-(3,4-Dimethoxybenzoyl)-1-piperazinylacetyl]carbostyril monohydrochloride 3/2-hydrate |
| 18 | 6-[4-(4-Methoxybenzoyl)-1-piperazinylacetyl]-carbostyril monohydrochloride 3/2-hydrate |
| 19 | 6-[4-(4-Methylbenzoyl)-1-piperazinylacetyl]-carbostyril monohydrochloride 3/2-hydrate |
| 20 | 6-(4-Benzoyl-1-piperazinylacetyl)carbostyril monohydrochloride 3/2-hydrate |
| 21 | 6-[4-(4-Cyanobenzoyl)-1-piperazinylacetyl]-carbostyril monohydrochloride 3/2-hydrate. |
| 22 | 6-[4-(3,4,5-Trimethoxybenzoyl)-1-piperazinylacetyl]carbostyril monohydrochloride 3/2-hydrate |
| 23 | 6-[4-(4-Nitrobenzoyl)-1-piperazinylacetyl]-carbostyril monohydrochloride ½-hydrate |
| 24 | 6-[4-(4-Methoxycinnamoyl)-1-piperazinylacetyl]-3,4-dihydrocarbostyril monohydrochloride monohydrate |
| 25 | 6-(4-Cinnamoyl-1-piperazinylacetyl)-3,4-dihydrocarbostyril monohydrochloride ½-hydrate |
| 26 | 6-[4-(4-Aminobenzoyl-1-piperazinylacetyl]-carbostyril dihydrochloride monohydrate |
| 27 | 6-[4-(2-Phenoxyethyl)-1-piperazinylacetyl]-3,4-dihydrocarbostyril dihydrochloride ½-hydrate |
| 28 | Amrinone: [3-Amino-5-(4-pyridinyl)-2(1H)—pyridinone] (Reference compound) |

PHARMACOLOGICAL TEST-1

Adult mongrel dogs of either sex, weighing 8–13 kg, were anesthetized with sodium petobarbital at a rate of 30 mg/kg by intraveneous administration. After another intraveneous administration of sodium heparin at a rate of 1,000 U/kg, the test dog was sacrificed by blood letting. The heart of the dog was excised and immediately plunged into Locke's solution, then the right coronary artery was cannulated to the atrinector artery and the right atrium was carefully isolated.

Next, the donor adult mongrel dogs of either sex, weighing 18–27 kg, were anesthtized with sodium pentobarbital at a rate of 30 mg/kg by intraveneous administration, and further treated with intraveneous administration of sodium heparin at a rate of 1,000 U/kg.

The above-mentioned right atrium perfused with the blood conducted from the carotid artery of the donor dog by aid of Peristaric pump. The perfusion pressure was maintained at 100 mm-Hg constantly. The movement of the right atrium was measured through a force-displacement transducer under a static tension of 2 g. The amount of blood flown in the coronary arteries was measured by electromagnetic flow meter.

All the data were recorded on an ink-writing recorder. [The method of this test was reported in an article written by Chiba et al., "Japan Journal of Pharmacology, 25, 433–439, (1975); Naunyn-Schmiedberg's Arch. Pharmacology, 289, 315–325, (1975)].

A solution containing a compound to be tested was injected into the artery through the rubber tube connected close to the cannula, in an amount of 10–30 microliters.

Positive inotropic effect of the compound to be tested is expressed as a percentage of the developed tension before and after the injection of the compound. The effect of the compound on blooed flow in coronary artery is expresses as an absolute value (ml/minutes) measured from before the injection of the compound. The results are shown in Table 3 below.

TABLE 3

| Compound No. | Dosage | Change of atrial muscle contraction (%) | Change of blood flow in coronary artery (ml/minute) |
|---|---|---|---|
| 1 | 1 μmol | 67.0 | 2.5 |
| 2 | 100 n mol | 20.7 | — |
| 3 | 100 n mol | 18.2 | — |
| 4 | 300 n mol | 25.0 | 1 |
| 5 | 1 μmol | — | 5 |
| 6 | 1 μmol | — | 8.5 |
| 7 | 1 μmol | — | 3.5 |
| 8 | 1 μmol | — | 3 |
| 9 | 1 μmol | 65.0 | 2 |
| 10 | 1 μmol | 112 | — |
| 11 | 1 μmol | 183 | 1.0 |
| 13 | 1 μmol | 86.7 | 3 |
| 14 | 1 μmol | 100 | 2.5 |
| 28 | 1 μmol | 57.5 | — |

PHARMACOLOGICAL TEST-2

Adult mongrel dogs of either sex, weighing 8–13 kg, were anesthetized with sodium pentobarbital at a rate of 30 mg/kg by intraveneous administration.

After another intraveneous administration of sodium heparin at a rate of 1,000 U/kg, the test dog was sacrificed by blood letting. The heart of the dog was excised, and the preparation was essentially consisting of the anterior papillary muscle and the venticular septum. The preparation was perfused through the cannulated anterior septal artery with the blood from the donor dog at a constant pressure of 100 mm-Hg. The dogs used as the donors were weighing 18–27 kg, and were anesthetized with pentobarbital sodium at a rate of 30 mg/kg by intraveneous administration, and further treated with intraveneous administration of sodium heparin at a rated of 1,000 U/kg. The papillary muscle was driven with rectangular pulse about 1.5-fold the threshold voltage (0.5–3 volts) and 5 seconds duration at a fixed rate of 120 beat/minute through bipolar pacing electrodes. Tension developed by the papillary muscle was measured by strain-gauge transducer. The muscle was loaded with a weight of about 1.5 g. Blood flow through the anterior septal artery was measure by an electromagnetic flow meter. Data developed tension and blood flow were recorded on charts with an ink-writing rectipgraph. [The detailed of this test method is reported in an article written by Endoh and Hashimoto, "Americal Journal of Physiology, 218, 1459–1463, (1970)".]

A compound to be tested was injected into the intraarterially in an amount of 10–30 μl in 4 seconds.

The inotropic effects of the compound are expressed as a percentage of the developed tension before and injection of the compounds.

The effect of the compound on blood flow are expressed as a difference (ml/minute) of the values before and after the injection of the compound. The results are shown in Table 4 below:

TABLE 4

| Compound No. | Dosage | Change of atrial muscle contraction (%) | Change of blood flow in coronary artery (ml/minute) |
|---|---|---|---|
| 5 | 1 μmol | 18.3 | 5.5 |
| 6 | 1 μmol | 16.1 | 9.0 |
| 7 | 1 μmol | 14.3 | 3.0 |
| 8 | 1 μmol | 19.8 | 3.5 |

TABLE 4-continued

| Compound No. | Dosage | Change of atrial muscle contraction (%) | Change of blood flow in coronary artery (ml/minute) |
|---|---|---|---|
| 12 | 100 n mol | 19.1 | 0.5 |
| 15 | 1 μmol | 23.1 | 3 |
| 16 | 1 μmol | 60.0 | 2.5 |
| 17 | 300 n mol | 27.1 | 1.5 |
| 18 | 100 n mol | 18.8 | 1 |
| 19 | 100 n mol | 23.1 | 1 |
| 20 | 100 n mol | 16.1 | 1 |
| 21 | 100 n mol | 17.4 | — |
| 22 | 100 n mol | 18 | 0.5 |
| 23 | 100 n mol | 28.8 | — |
| 24 | 1 μmol | 17 | 1 |
| 25 | 1 μmol | 12.9 | 1 |
| 26 | 1 μmol | 18.7 | 1.5 |
| 27 | 100 n mol | 12 | 3 |
| 28 | 1 μmol | 31.6 | — |

PHARMACOLOGICAL TEST-3

Mongrel dogs of either sex, weighing 9-15 kg, were anesthtized with sodium pentabarbital initially in a dosage of 30 mg/kg intraveneously and sequently at a rate of 4 mg/kg/hr intraveneously by using an infusion pump. The animals were respired with room air in a tidal volume of 20 ml/kg at a rate of 18 beats/minute by using respirator.

The chest was opened by a midleline incision and the heart was suspended in the pericardial cradle.

The contractile force of the myocardium was measured by means of a Walton-Brodie type strain-gauge arch sutured onto the left ventricle. Systemic blood pressure was measure from the left femoral artery by a pressure transducer, and the heat rate was measured by a cardiotachometer triggered by blood pressure pulses.

All the data were recorded on charts by use of a rectilinear recorder.

A compound to be tested was injected into the left femoral vein.

The inotropic effects of the compound are expressed as a percentage of the developed tension before the injection of the compound.

The effect of the compound on the blood pressure (mm-Hg) or heat rate (beat/minute) is expressed as a difference between the values before and after the injection of the compound. The results are shown in Table 5 below:

TABLE 5

| Compound No. | Dosage (mg/kg) | Change of contriction of left venticle (%) | Blood pressure (mm-Hg) Diostasis | Systole | Heart rate (beat/min) |
|---|---|---|---|---|---|
| 1 | 1 | 44 | −28 | −16 | −8 |
| 11 | 1 | 57.1 | −12 | −6 | −3 |
| 16 | 1 | 55 | −10 | −18 | 0 |
| Dobutamine (Reference compound) | 0.01 | 68 | −28 | 36 | 34 |

Examples of cardiotonic compositions containing carbostyril derivative represented by the general formula (1) of the present invention as the active ingredient are shown as follows:

EXAMPLE OF PREPARATION OF TABLES-1

By using an usual procedure, tablets having the following formulation were prepared.

| 6-[4-(4-Methylbenzoyl)-1-piperazinylacetyl]-3,4-dihydrocarbostyril monohydrochloride monohydrate | 5 mg |
|---|---|
| Starch | 132 mg |
| Magnesium stearate | 18 mg |
| Lactose | 45 mg |
| | 200 mg |

EXAMPLE OF PREPARATION OF TABLETS-2

By using an usual procedure, tablets having the following formulation were prepared.

| 6-[4-(3,4,5-Trimethoxy-benzoyl)-1-piperzinyl-acetyl]-3,4-dihydrocarbostyril | 10 mg |
|---|---|
| Starch | 127 mg |
| Magnesium stearate | 18 mg |
| Lactose | 45 mg |
| | 200 mg |

EXAMPLE OF PREPARATION OF INJECTIONS

| 6-[4-(4-Nitrobenzoyl)-1-piperazinylacetyl]-3,4-dihydrocarbostyril | 500 mg |
|---|---|
| Polyethylene glycol [Molecular weight: 4,000] | 0.3 g |
| Sodium chloride | 0.9 g |
| Polyoxyethylene sorbitan monooleate | 0.4 g |
| Sodium metabisulfite | 0.1 g |
| Methyl p-hydroxybenzoate | 0.18 g |
| Propyl p-hydroxybenzoate | 0.02 g |
| Distilled water for injection | 100 ml |

Above prescribed methyl p-hydroxybenzoate, propyl p-hydroxybenzoate, sodium metabisulfite and sodium chloride were dissolved in distilled water at 80° C. under stirring. The obtained solution was cooled to 40° C., and then into this solution was added compound of the present invention, polyethylene glycol and polyoxyethylene sorbitan monooleate in this order. This obtained solution was diluted with distilled water for injection to the final regulated volume and then sterilized by using a suitable filter paper for sterilization. One milliliter each of the obtained solution was filled in an ampoule separately to make injection preparations.

EXAMPLE OF PREPARATION OF TABLETS-3

By using an usual procedure, tablets having the formulation were prepared as follows:

| 6-[4-(3,4,5-Trimethoxybenzoyl)-1-piperazinylacetyl]carbostyril monohydrochloride 3/2-hydrate | 10 mg |
|---|---|
| Starch | 127 mg |
| Magnesium stearate | 18 mg |
| Lactose | 45 mg |
| | 200 mg |

What is claimed is:

1. A carbostyril derivative or a pharmaceutically acceptable salt thereof, said derivative being represented by the formula (1),

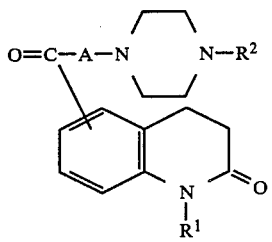
(1)

wherein $R^1$ is a hydrogen atom, a lower alkyl group, a lower alkenyl group, a lower alkynyl group or a phenyl-lower alkyl group; $R^2$ is a lower alkanoyl group, a lower alkoxycarbonyl group, a furoyl group, a lower alkane-sulfonyl group, a benzoyl group (which benzoyl group may have (a) 1 to 3 substituents on the phenyl ring selected from the group consisting of a lower alkyl group, a lower alkoxy group, a halogen atom, and an amino group, (b) 1 substituent on the phenyl ring selected from the group consisting of a nitro group and a cyano group or (c) a lower alkylenedioxy group as the substituent on the phenyl ring), a phenyl-lower alkenyl-carbonyl group (which may have 1 to 3 lower alkoxy groups as the substituents on the phenyl ring), a phenoxy-lower alkyl group, or a phenylsulfonyl group (which may have a lower alkyl group as the substituent on the phenyl ring); A is a lower alkylene group; the carbon-carbon bond between the 3- and 4-positions in the carbostyril skeleton is a single or double bond; and the substituted position of the side-chain of the formula,

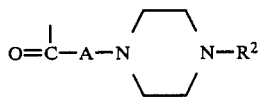

may be any one of the 5-, 6-, 7- or 8-positions in the carbostyril skeleton.

2. The carbostyril derivative or pharmaceutically acceptable salt thereof according to claim 1, wherein the carbostyril derivative is represented by the general formula,

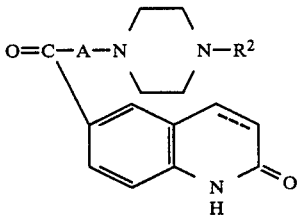

wherein $R^2$ is a lower alkanoyl group, a lower alkoxy-carbonyl group, a furoyl group, a lower alkanesulfonyl group, a benzoyl group (which benzoyl group may have (a) 1 to 3 substituents on the phenyl ring selected from the group consisting of a lower alkyl group, a lower alkoxy group, a halogen atom, and an amino group, (b) 1 substituent on the phenyl ring selected from the group consisting of a nitro group and a cyano group or (c) a lower alkylenedioxy group as the substituent on the phenyl ring), a phenyl-lower alkenylcarbonyl group (which may have 1 to 3 lower alkoxy group as the substituents on the phenyl ring), a phenoxy-lower alkyl group, or a phenylsulfonyl group (which may have a lower alkyl group as the substituent on the phenyl ring); A is a lower alkylene group, the carbon-carbon bond between the 3- and 4-positions in the carbostyril skeleton is a single or double bond; and the substituted position of the side-chain of the formula,

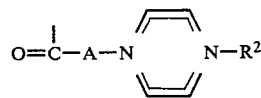

is the 6-position in the carbostyril skeleton.

3. The carbostyril derivative or pharmaceutically acceptable salt thereof according to claim 1, wherein $R^2$ is a phenyl-lower alkenylcarbonyl group (which may have 1 to 3 lower alkoxy group as the substituents on the phenyl ring), or a phenoxy-lower alkyl group.

4. The carbostyril derivative or pharmaceutically acceptable salt thereof according to claim 1, wherein $R^1$ is a lower alkyl group, a lower alkenyl group, a lower alkynyl group or a phenyl-lower alkyl group; and $R^2$ is a lower alkanoyl group, a lower alkoxycarbonyl group, a furoyl group, a lower alkanesulfonyl group, a benzoyl group (which benzoyl group may have (a) 1 to 3 substituents on the phenyl ring selected from the group consisting of a lower alkyl group, a lower alkoxy group, a halogen atom, and an amino group, (b) 1 substituent on the phenyl ring selected from the group consisting of a nitro group and a cyano group or (c) a lower alkylenedioxy group as the substituent on the phenyl ring), or a phenylsulfonyl group (which may have a lower alkyl group as the substituent on the phenyl ring).

5. The carbostyril derivative or pharmaceutically acceptable salt thereof according to claim 1, wherein $R^1$ is a hydrogen atom; $R^2$ is a lower alkanoyl group, a lower alkoxycarbonyl group, a furoyl group, a lower alkanesulfonyl group, a benzoyl group (which benzoyl group may have (a) 1 to 3 substituents on the phenyl ring selected from the group consisting of a lower alkyl group, a lower alkoxy group, a halogen atom, and an amino group, (b) 1 substituent on the phenyl ring selected from the group consisting of a nitro group and a cyano group or (c) a lower alkylenedioxy group as the substituent on the phenyl ring), a phenylsulfonyl group (which may have a lower alkyl group as the substituent on the phenyl ring); and the substituted position of the side-chain of the formula,

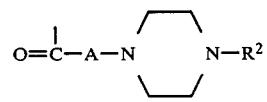

may be any one of the 5-, 7- or 8-positions in the carbostyril skeleton.

6. The carbostyril derivative or pharmaceutically acceptable salt thereof according to claim 2, wherein $R^2$ is a benzoyl group (which benzoyl group may have (a) 1 to 3 substituents selected from the group consisting of a lower alkyl group, a lower alkoxy group, a halogen atom, and an amino group, (b) 1 substituent on the phenyl ring selected from the group consisting of a nitro group and a cyano group or (c) a lower alkylenedioxy group as the substituent on the phenyl ring).

7. The carbostyril derivative or pharmaceutically acceptable salt thereof according to claim 2, wherein $R^2$ is a lower alkanoyl group, a lower alkoxycarbonyl group, a furoyl group, a lower alkanesulfonyl group, or a phenylsulfonyl group (which may have a lower alkyl group as the substituent on the phenyl ring).

8. The carbostyril derivative or pharmaceutically acceptable salt thereof according to claim 3, wherein $R^1$ is a halogen atom, and the substituted position of the side-chain of the formula,

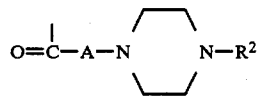

is the 6-position in the carbostyril skeleton.

9. The carbostyril derivative or pharmaceutically acceptable salt thereof according to claim 5, wherein $R^2$ is a benzoyl group (which benzoyl group may have (a) 1 to 3 substituents on the phenyl ring selected from the group consisting of a lower alkyl group, a lower alkoxy group, a halogen atom, and an amino group, (b) 1 substituent on the phenyl ring selected from the group consisting of a nitro group and a cyano group or (c) a lower alkylenedioxy group as the substituent on the phenyl ring).

10. The carbostyril derivative or pharmaceutically acceptable salt thereof according to claim 6, wherein the carbon-carbon bond between the 3- and 4-positions in the carbostyril skeleton is a single bond.

11. The carbostyril derivative or pharmaceutically acceptable salt thereof according to claim 6, wherein the carbon-carbon bond between the 3- and 4-positions in the carbostyril skeleton is a double bond.

12. 6-[4-(3,4-Dimethoxybenzoyl)-1-piperazinylacetyl]-3,4-dihydrocarbostyril.

13. 6-[4-(3-Chlorobenzoyl)-1-piperazinylacetyl]-3,4-dihydrocarbostyril.

14. 6-[4-(4-Methylbenzoyl)-piperazinylacetyl]-3,4-dihydrocarbostyril.

15. 6-[4-(3,4-Methylenedioxybenzoyl)-1-piperazinylacetyl]-3,4-dihydrocarbostyril.

16. 6-[4-(3-Chlorobenzoyl)-1-piperazinylacetyl]-carbostyril.

17. A cardiotonic composition containing a carbostyril derivative or a pharmaceutically acceptable salt thereof, said derivative being represented by the formula (1) as claimed in claim 1 or 2, as the active ingredient.

* * * * *

UNITED STATES PATENT AND TRADEMARK OFFICE
CERTIFICATE OF CORRECTION

PATENT NO. : 4,514,401
DATED : April 30, 1985
INVENTOR(S) : Michiaki Tominaga et al.

It is certified that error appears in the above-identified patent and that said Letters Patent is hereby corrected as shown below:

Claim 2, column 40, line 15:

Delete the formula and insert:

Page 1, box [63]:

Delete "Continuation of Ser. No. 265,501, May 20, 1981, abandoned."

Signed and Sealed this

Fifth Day of November 1985

[SEAL]

Attest:

DONALD J. QUIGG

Attesting Officer

Commissioner of Patents and Trademarks